United States Patent [19]

Lau et al.

[11] Patent Number: 5,604,253
[45] Date of Patent: Feb. 18, 1997

[54] N-BENZYLINDOL-3-YL PROPANOIC ACID DERIVATIVES AS CYCLOOXYGENASE INHIBITORS

[75] Inventors: Cheuk K. Lau, Ile Bizard; Cameron Black, Pointe Claire; Daniel Guay, Ile Perrot; Jacques Y. Gauthier, Laval; Yves LeBlanc, Kirkland; Patrick Roy, Dollard des Ormeaux; Yves Ducharme, Montreal; Pierre Hamel, Laval, all of Canada

[73] Assignee: Merck Frosst Canada, Inc., Kirkland, Canada

[21] Appl. No.: 445,624

[22] Filed: May 22, 1995

[51] Int. Cl.⁶ .................. A61K 31/405; C07D 209/04; C07D 209/10
[52] U.S. Cl. .................. 514/415; 548/469; 548/494; 548/509; 548/510
[58] Field of Search .................. 514/415; 548/469, 548/494, 509, 510

[56] References Cited

U.S. PATENT DOCUMENTS

| | | | |
|---|---|---|---|
| 3,161,654 | 12/1964 | Shen | 548/500 |
| 3,196,162 | 7/1965 | Sarett et al. | 548/403 |
| 3,242,163 | 3/1966 | Sarett et al. | 536/55 |
| 3,654,349 | 4/1972 | Shen et al. | 562/428 |
| 3,725,548 | 4/1973 | Shen et al. | 514/517 |

FOREIGN PATENT DOCUMENTS

| | | |
|---|---|---|
| 709844 | 5/1965 | Canada . |
| 709843 | 5/1965 | Canada . |
| 957990 | 5/1964 | United Kingdom . |
| 2225012 | 5/1990 | United Kingdom . |
| WO94/06769 | 3/1994 | WIPO . |

OTHER PUBLICATIONS

Chem. Abstracts, vol. 61, p. 4320 (a) (1964) "Resolution of Substituted Indoles" 1–p–chlorobenzyl–2–methyl–5–methoxy–3–indolyl)propionic acid.

*Primary Examiner*—Thomas Hamilton, III
*Attorney, Agent, or Firm*—Curtis C. Panzer; David L. Rose

[57] ABSTRACT

The invention encompasses the novel compound of Formula I as well as a method of treating cyclooxygenase-2 mediated diseases comprising administration to a patient in need of such treatment of a non-toxic therapeutically effective amount of a compound of Formula I.

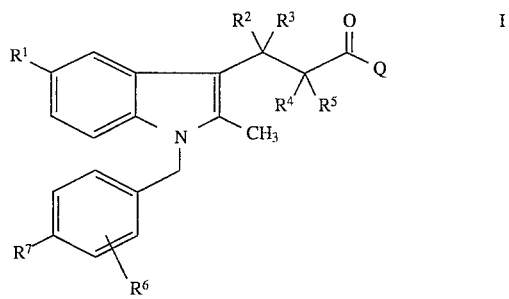

The invention also encompasses certain pharmaceutical compositions for treatment of cyclooxygenase-2 mediated diseases comprising compounds of Formula I.

16 Claims, No Drawings

N-BENZYLINDOL-3-YL PROPANOIC ACID DERIVATIVES AS CYCLOOXYGENASE INHIBITORS

BACKGROUND OF THE INVENTION

This invention relates to methods of treating cyclooxygenase mediated diseases and certain pharmaceutical compositions therefor.

Non-steroidal, anti-inflammatory drugs exert most of their anti-inflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 or the constitutive enzyme, as originally identified in bovine seminal vesicles. More recently the gene for a second inducible form of cyclooxygenase (cyclooxygenase-2) has been cloned, sequenced and characterized initially from chicken, murine and human sources. This enzyme is distinct from the cyclooxygenase-1 which has been cloned, sequenced and characterized from various sources including the sheep, the mouse and man. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar anti-inflammatory, antipyretic and analgesic properties to a conventional non-steroidal anti-inflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Such a compound would also be of use in the treatment of Alzheimer's disease and to inhibit bone resorption (for use in the treatment of osteoporosis).

A brief description of the potential utility of cyclooxygenase-2 is given in an article by John Vane, Nature, Vol. 367, pp. 215–216, 1994.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

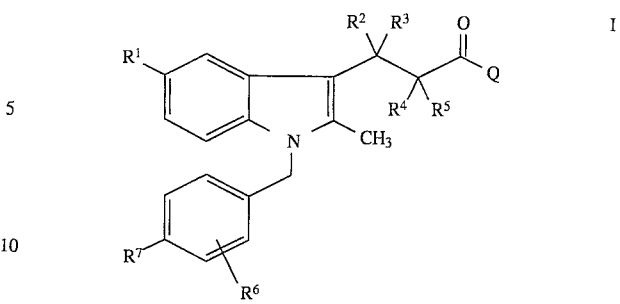

The invention also encompasses certain pharmaceutical compositions for treatment of cyclooxygenase-2 mediated diseases comprising compounds of Formula I.

DETAILED DESCRIPTION OF THE INVENTION

In one embodiment the invention encompasses the novel compound of Formula I as well as a method of treating cyclooxygenase-2 mediated diseases comprising administration to a patient in need of such treatment of a non-toxic therapeutically effective amount of a compound of Formula I.

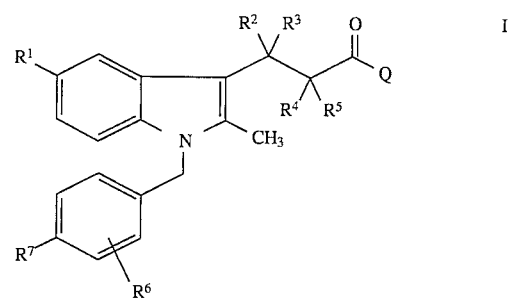

or a pharmaceutically acceptable salt thereof, wherein:

Q is
  (a) —OR or
  (b) —NR$^9$R$^{10}$;

R is
  (a) —H or
  (b) —C$_{1-4}$ alkyl;

R$^1$ is
  (a) —OCH$_3$,
  (b) —OCH$_2$F,
  (c) —OCHF$_2$,
  (d) F, Cl, Br or I, or
  (e) methyl or ethyl;

R$^2$, R$^3$, R$^4$ and R$^5$ are independently
  (a) —H,
  (b) —F,
  (c) methyl or ethyl,
  (d) —CF$_3$, CF$_2$H, or CFH$_2$,
  (e) —OH, OR$^8$, SR$^8$, S(O)R$^8$, or S(O)$_2$R$^8$,
  (f) mono- or di-substituted benzyl, wherein the substituent is selected from
    (1) hydrogen,
    (2) CF$_3$,
    (3) CN,
    (4) F, Cl, Br or I,
    (5) C$_{1-6}$alkyl,
    (6) SR$^8$, S(O)R$^8$, or S(O)$_2$R$^8$,
  (g) naphthylmethyl;
or R$^2$ together with R$^3$ form an oxo group;

or $R^4$ together with $R^5$ form an oxo group;

or $R^2$ and $R^3$ are joined so that together with the carbon atom to which they are attached there is formed a saturated monocyclic hydrocarbon ring of 3, 4, 5, 6 or 7 members;

or $R^2$ and $R^4$ are joined so that together with the carbon atoms to which they are attached there is formed a saturated monocyclic hydrocarbon ring of 3, 4, 5, 6 or 7 members;

or $R^2$ and $R^5$ are joined so that together with the carbon atoms to which they are attached there is formed a saturated monocyclic hydrocarbon ring of 3, 4, 5, 6 or 7 members;

or $R^3$ and $R^4$ are joined so that together with the carbon atoms to which they are attached there is formed a saturated monocyclic hydrocarbon ring of 3, 4, 5, 6 or 7 members;

or $R^3$ and $R^5$ are joined so that together with the carbon atoms to which they are attached there is formed a saturated monocyclic hydrocarbon ring of 3, 4, 5, 6 or 7 members;

or $R^4$ and $R^5$ are joined so that together with the carbon atom to which they are attached there is formed a saturated monocyclic hydrocarbon ring of 3, 4, 5, 6 or 7 members;

$R^6$ is H or F;

$R^7$ is
  (a) Br, Cl or I,
  (b) SMe, SEt, or $SCF_2H$;

$R^8$ is methyl, ethyl or mono- or di-substituted benzyl, wherein the substituent is selected from
  (1) hydrogen,
  (2) $CF_3$,
  (3) CN,
  (4) F, Cl, Br or I,
  (5) $C_{1-6}$alkyl;

$R^9$ and $R^{10}$ are independently
  (a) —H,
  (b) —$C_{1-3}$ alkyl,
  (c) —OR,
  (d) —$C(O)R^{11}$,
  (e) —$S(O)_2R^{12}$,
  (f) mono-substituted $C_{2-4}$ alkyl wherein the substituent is selected from
    (1) hydroxy,
    (2) amino,
    (3) methylamino, and
    (4) dimethylamino, provided that said substituent is located on a carbon of $C_{2-4}$ alkyl other than the one attached to the nitrogen of —$NR^9R^{10}$,
  (g) phenyl, benzyl or pyridyl optionally mono- or di-substituted, the substituents being selected from the group consisting of
    (1) hydrogen,
    (2) $CF_3$,
    (3) CN,
    (4) F, Cl, Br or I,
    (5) $C_{1-6}$alkyl;

or $R^9$ and $R^{10}$ are joined so that together with the nitrogen atom to which they are attached there is formed a saturated or unsaturated monocyclic ring of 3, 4, 5, 6, or 7 members, optionally containing one or two additional heteroatoms, said heteroatoms independently selected from N, O and S, said ring optionally containing one or two carbonyl or sulfonyl groups;

$R^{11}$ is
  (a) H,
  (b) —$C_{1-4}$ alkyl,
  (c) —$CF_3$,
  (d) phenyl or benzyl optionally mono- or di-substituted, the substituents being selected from the group consisting of
    (1) hydrogen,
    (2) $CF_3$,
    (3) CN,
    (4) F, Cl, Br or I,
    (5) $C_{1-6}$alkyl;

$R^{12}$ is
  (a) —$C_{1-4}$ alkyl,
  (b) —$CF_3$,
  (c) phenyl or benzyl optionally mono- or di-substituted, the substituents being selected from the group consisting of
    (1) hydrogen,
    (2) $CF_3$,
    (3) CN,
    (4) F, Cl, Br or I,
    (5) $C_{1-6}$alkyl;

with the proviso that when Q is OR and $R^1$ is OMe and $R^2$, $R^3$, $R^4$, $R^5$ and $R^6$ are simultaneously hydrogen, $R^7$ is other than Cl.

Within the definition of Q, some representative radicals are:

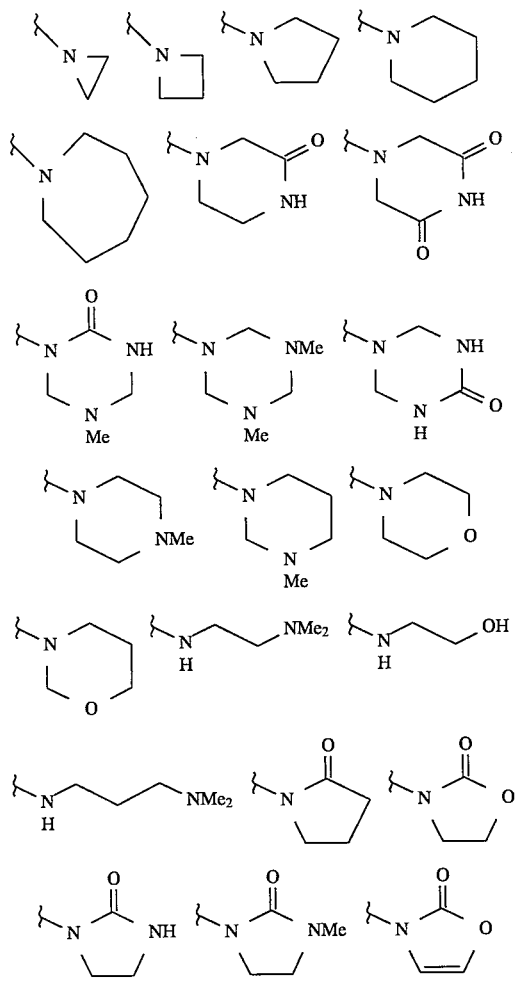

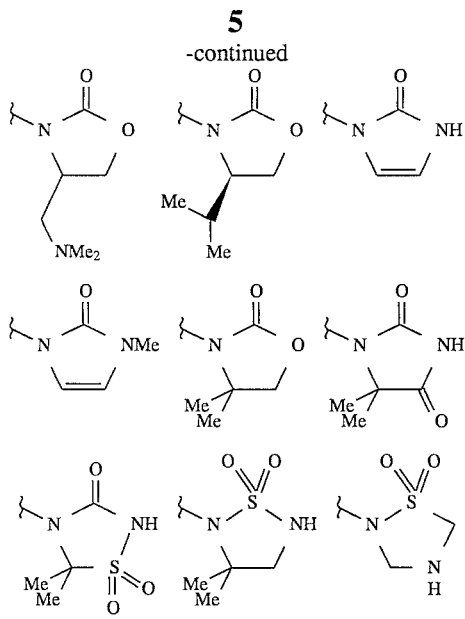

Within this embodiment there is a genus of compounds of formula I wherein

Q is
(a) —OR or
(b) —NR$^9$R$^{10}$;

R is
(a) —H or
(b) —C$_{1-4}$ alkyl;

R$^1$ is
(a) —OCH$_3$,
(b) —OCH$_2$F,
(c) —OCHF$_2$,
(d) F, Cl, Br or I, or
(e) methyl or ethyl;

R$^2$ and R$^3$ are independently
(a) —H,
(b) —F,
(c) methyl or ethyl,
(d) —CF$_3$,
(e) —OH or SR$^8$, R$^4$ and R$^5$ are independently
(a) —H,
(b) methyl or ethyl,
(c) —OH or SR$^8$,
(f) mono- or di-substituted benzyl, wherein the substituent is selected from
(1) hydrogen,
(2) CF$_3$,
(3) CN,
(4) F, Cl, Br or I,
(5) C$_{1-6}$alkyl,
(6) SR$^8$, S(O)R$^8$ or S(O)$_2$R$^8$,
(g) naphthylmethyl, or R$^2$ and R$^3$ are joined so that together with the carbon atom to which they are attached there is formed a saturated monocyclic hydrocarbon ring of 3, 4, 5, 6 or 7 members;

or R$^3$ and R$^4$ are joined so that together with the carbon atoms to which they are attached there is formed a saturated monocyclic hydrocarbon ring of 3, 4, 5, 6 or 7 members;

R$^6$ is H or F;

R$^7$ is
(a) Br, Cl or I,
(b) SMe, SEt, or SCF$_2$H;

R$^8$ is methyl, ethyl or mono- or di-substituted benzyl, wherein the substituent is selected from
(1) hydrogen,
(2) CF$_3$,
(3) CN,
(4) F, Cl, Br or I,
(5) C$_{1-6}$alkyl;

R$^9$ is hydrogen or methyl;

R$^{10}$ is
(a) —H,
(b) —C$_{1-3}$ alkyl,
(c) —OR,
(d) —C(O)R$^{11}$,
(e) —S(O)$_2$R$^{12}$,
(f) mono-substituted C$_{2-4}$ alkyl wherein the substituent is selected from
(1) hydroxy,
(2) amino,
(3) methylamino, and
(4) dimethylamino, provided that said substituent is located on a carbon of C$_{2-4}$ alkyl other than the one attached to the nitrogen of —NR$^9$R$^{10}$
(g) phenyl, benzyl or pyridyl optionally mono- or di-substituted, the substituents being selected from the group consisting of
(1) hydrogen,
(2) CF$_3$,
(3) CN,
(4) F, Cl, Br or I,
(5) C$_{1-4}$alkyl;

R$^{11}$ is
(a) H,
(b) —C$_{1-4}$ alkyl,
(c) —CF$_3$,
(d) phenyl or benzyl optionally mono- or di-substituted, the substituents being selected from the group consisting of
(1) hydrogen,
(2) CF$_3$,
(3) CN,
(4) F, Cl, Br or I,
(5) C$_{1-6}$alkyl;

R$^{12}$ is
(a) —C$_{1-4}$ alkyl,
(b) —CF$_3$,
(c) phenyl or benzyl optionally mono- or di-substituted, the substituents being selected from the group consisting of
(1) hydrogen,
(2) CF$_3$,
(3) CN,
(4) F, Cl, Br or I,
(5) C$_{1-6}$alkyl.

Within this genus there is a class of compounds of formula I wherein

Q is
(a) —OR or
(b) —NR$^9$R$^{10}$;

R is
(a) —H or
(b) —C$_{1-4}$ alkyl;

R$^1$ is
(a) —OCH$_3$,
(b) —OCH$_2$F,
(c) —OCHF$_2$,
(d) F, Cl, Br or I, (e) methyl or ethyl;

$R^2$ and $R^3$ are independently
- (a) —H,
- (b) —F,
- (c) methyl or ethyl,
- (d) —$CF_3$,
- (e) —OH or $SR^8$, $R^4$ is
- (a) —H,
- (b) methyl or ethyl,
- (c) —OH or $SR^8$,
- (f) mono- or di-substituted benzyl, wherein the substituent is selected from
  - (1) hydrogen,
  - (2) $CF_3$,
  - (3) CN,
  - (4) F, Cl, Br or I,
  - (5) $C_{1-4}$alkyl,
  - (6) $SR^8$, $S(O)R^8$, or $S(O)_2R^8$,
- (g) naphthylmethyl, or $R^2$ and $R^3$ are joined so that together with the carbon atom to which they are attached there is formed a saturated monocyclic hydrocarbon ring of 3, 4, 5, 6 or 7 members;

or $R^3$ and $R^4$ are joined so that together with the carbon atoms to which they are attached there is formed a saturated monocyclic hydrocarbon ring of 3, 4, 5, 6 or 7 members;

$R^5$ is H or methyl;

$R^6$ is H or F;

$R^7$ is
- (a) Br, Cl or I,
- (b) SMe, SEt, or $SCF_2H$;

$R^8$ is methyl, ethyl or mono- or di-substituted benzyl, wherein the substituent is selected from
- (1) hydrogen,
- (2) $CF_3$,
- (3) CN,
- (4) F, Cl, Br, or I,
- (5) $C_{1-4}$alkyl;

$R^9$ is hydrogen or methyl;

$R^{10}$ is
- (a) —H,
- (b) —$C_{1-3}$ alkyl,
- (c) —OR,
- (d) —$C(O)R^{11}$,
- (e) —$S(O)_2R^{12}$,
- (f) phenyl, benzyl or pyridyl optionally mono- or di-substituted, the substituents being selected from the group consisting of
  - (1) hydrogen,
  - (2) $CF_3$,
  - (3) CN,
  - (4) F, Cl, Br or I,
  - (5) $C_{1-4}$alkyl;

$R^{11}$ is
- (a) H,
- (b) —$C_{1-4}$ alkyl,
- (c) —$CF_3$,
- (d) phenyl or benzyl optionally mono- or di-substituted, the substituents being selected from the group consisting of
  - (1) hydrogen,
  - (2) $CF_3$,
  - (3) CN,
  - (4) F, Cl, Br or I,
  - (5) $C_{1-4}$alkyl;

$R^{12}$ is
- (a) —$C_{1-4}$ alkyl,
- (b) —$CF_3$,
- (c) phenyl or benzyl optionally mono- or di-substituted, the substituents being selected from the group consisting of
  - (1) hydrogen,
  - (2) $CF_3$,
  - (3) CN,
  - (4) F, Cl, Br or I,
  - (5) $C_{1-4}$alkyl;

Within this class there is a sub-class of compounds of formula I wherein

Q is
- (a) —OR or
- (b) —$NR^9R^{10}$;

R is
- (a) —H or
- (b) —$C_{1-3}$ alkyl;

$R^1$ is
- (a) —$OCH_3$,
- (b) —$OCH_2F$,
- (c) —$OCHF_2$,
- (d) F, Cl, Br or I,
- (e) methyl or ethyl;

$R^2$ and $R^3$ are independently
- (a) —H,
- (b) —F,
- (c) methyl or ethyl,
- (d) —$CF_3$,
- (e) —OH or $SR^8$, $R^4$ is
- (a) —H,
- (b) methyl or ethyl,
- (c) —OH or $SR^8$,
- (f) mono- or di-substituted benzyl, wherein the substituent is selected from
  - (1) hydrogen,
  - (2) $CF_3$,
  - (3) CN,
  - (4) F, Cl, Br or I,
  - (5) $C_{1-3}$alkyl,
  - (6) $SR^8$, $S(O)R^8$, or $S(O)_2R^8$,
- (g) naphthylmethyl, or $R^2$ and $R^3$ are joined so that together with the carbon atom to which they are attached there is formed a saturated monocyclic hydrocarbon ring of 3, 4, 5, 6 or 7 members;

or $R^3$ and $R^4$ are joined so that together with the carbon atoms to which they are attached them is formed a saturated monocyclic hydrocarbon ring of 3, 4, 5, 6 or 7 members;

$R^5$ is H or methyl;

$R^6$ is H or F;

$R^7$ is
- (a) Br, Cl or I,
- (b) SMe, SEt, or $SCF_2H$;

$R^8$ is methyl, ethyl or mono- or di-substituted benzyl, wherein the substituent is selected from
- (1) hydrogen,
- (2) $CF_3$,
- (3) CN,
- (4) F, Cl, Br or I,
- (5) $C_{1-3}$alkyl;

$R^9$ is hydrogen or methyl;

$R^{10}$ is (a) —H,
(b) —$C_{1-3}$ alkyl,
(c) —OR,
(d) —C(O)$R^{11}$,
(e) —S(O)$_2R^{12}$, $R^{11}$ is
(a) H,
(b) —$C_{1-3}$ alkyl,
(c) —$CF_3$,
(d) phenyl or benzyl optionally mono- or di-substituted, the substituents being selected from the group consisting of
  (1) hydrogen,
  (2) $CF_3$,
  (3) CN,
  (4) F, Cl, Br or I,
  (5) $C_{1-4}$alkyl;

$R^{12}$ is
(a) —$C_{1-3}$ alkyl,
(b) —$CF_3$,
(c) phenyl or benzyl optionally mono- or di-substituted, the substituents being selected from the group consisting of
  (1) hydrogen,
  (2) $CF_3$,
  (3) CN,
  (4) F, Cl, Br or I,
  (5) $C_{1-3}$alkyl;

Within this sub-class there are the compounds of formula I wherein

Q is
(a) —OH or
(b) —$NH^2$;
(c) NHS(O)$_2$Me;

R is
(a) —H or
(b) methyl, ethyl or propyl;

$R^1$ is
(a) —$OCH_3$,
(b) Cl or Br, $R^2$ and $R^3$ are independently
(a) —H,
(b) methyl,
(c) —$CF_3$, $R^4$ is
(a) —H,
(b) methyl,
(c) benzyl, or $R^2$ and $R^3$ are joined so that together with the carbon atom to which they are attached there is formed a saturated monocyclic hydrocarbon ring of 3 members;

or $R^3$ and $R^4$ are joined so that together with the carbon atoms to which they are attached there is formed a saturated monocyclic hydrocarbon ring of 3 members;

$R^5$ is H or methyl;
$R^6$ is H;
$R^7$ is Br,
$R^9$ is hydrogen;
$R^{10}$ is H,
$R^{12}$ is
(a) —$C_{1-3}$ alkyl,
(b) —$CF_3$.

Optical Isomers—Diastereomers—Geometric Isomers optical isomers. The present invention is meant to comprehend such possible diastereomers as well as their racemic and resolved, enantiomerically pure forms and pharmaceutically acceptable salts thereof.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease and for decreasing bone loss in postmenopausal women (that is, treatment of osteoporosis).

By virtue of its high cyclooxygenase-2 (COX-2) activity and/or its specificity for cyclooxygenase-2 over cyclooxygenase-1 (COX-1), compound I will prove useful as an alternative to conventional non-steroidal anti-inflammatory drags (NSAID'S) particularly where such non-steroidal anti-inflammatory drags may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, compound I will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapemane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

Pharmaceutical Compositions

For the treatment of any of these cyclooxygenase mediated diseases compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example, peanut oil, liquid paraffin, or olive oil.

Aqueous suspensions contain the active material in admixture with excipients suitable for the manufacture of aqueous suspensions. Such excipients are suspending agents, for example, sodium carboxymethyl-cellulose, methylcellulose, hydroxypropylmethycellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carder materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

The compounds of the present invention can be prepared according to the following methods:

Method A

An aryl hydrazine II and a methyl ketone III are coupled via a Fischer indole synthesis in acetic acid at 60° C. to 100° C. or alternatively in 4M HCl in dioxane at 60° C. or alternatively in ethanolic HCl at reflux. The indole IV thus obtained may be benzylated by first deprotonating with KHMDS in THF/HMPA at −78° C. to 0° C. or alternatively with sodium hydride in DMF at room temperature, followed by treatment with a benzyl halide V to provide N-benzylated indole Ib. In the case of R=H in compound IV, the benzylation may be accomplished by treatment of IV in THF/HMPA at −78° C. with two equivalents of n-BuLi followed by addition of benzyl halide V, to directly afford examples of compound Ia. In the case of a benzylated indole VI without α-substituents (a special case of IV in which $R^4$=$R^5$=H), an α-substituent may be introduced by enolization with LDA at −78° C. to 0° C. followed by treatment with an alkyl halide to provide VII. A second substituent may be similarly introduced to compound VII by sequential treatment with LDA and an alkyl halide to provide Ib. Compounds Ib and VII are examples of the present invention. Alkaline hydrolysis of esters Ib or VII provide examples of compound Ia of the present invention.

Method B

A substituted indole VIII may be formylated in the 3-position with DMF/POCl$_3$ to provide compound IX ($R^2$=H). Alternatively, VIII may be acylated using an appropriate anhydride or acid chloride to provide compound IX. For certain acylating agents, the addition of a Lewis acid catalyst (exemplified by AlCl$_3$) may be required for this reaction to proceed. Compound IX may be benzylated by treatment with V in DMF in the presence of sodium hydride to provide compound X. This compound may be reacted with a stabilized Wittig reagent XI in refluxing toluene to provide compound XII. For certain $R^2$ and $R^4$ groups, elevated pressure (>2000 psi) and elevated temperature (>140° C.) may be required for this reaction to proceed. Treatment of XII with a lithium dialkyl cuprate in the presence of TMSCl provides the alkylated product VII. Alternatively, XII may be treated with 50 psi H$_2$ in the presence of PtO$_2$ to provide compound XIII. Esters VII and XIII are examples of compound Ib of this invention, and hydrolysis of them provides examples of acid Ia of the present invention.

Method C

Benzylated indole X may be reacted with the ylid formed from methyl triphenylphosphonium bromide and potassium tert-butoxide to give the olefin XIV. Tetra-acyloxy rhodium catalyzed cyclopropanation of XIV with an α-diazoester XV at room temperature provides compound XVI, which can be hydrolyzed to give compound XVII. Both XVI and XVII are representative examples of Ib and Ia.

Method D

Benzylated indole X may be reacted with an enolate obtained by treatment of ester XVIII with LDA at −78° C. to provide the aldol adduct XIX. The hydroxyl group of this aldol adduct may be derivatized by treatment with electrophilic alkylating agents exemplified by Me$_3$OBF$_4$, to give the methyl ether XXI, and a substituted benzyl trichloroacetimidate XX, to give benzyl ether XXII. Subsequent alkaline hydrolysis of compounds XXI and XXII will provide compounds XXIII and XXIV respectively; these four compounds are examples of the present invention.

Method E

The cyclopropyl alcohol XXV (Eur. Pat. 604,114, Example 1, Step 7, Case 18907) may be oxidized under the conditions of Swern to aldehyde XXVI. Treatment of this aldehyde with Ph$_3$P=CHOMe, followed by hydrolysis of the resulting vinyl methyl ether will provide aldehyde XXVII. Addition of methyl magnesium bromide to this aldehyde followed by Swern oxidation of the resulting alcohol will provide methyl ketone XXVIII. Hydrazine II may be benzylated by treatment with benzyl bromide V in the presence of a base such as potassium carbonate to provide N-benzyl hydrazine XXIX. This hydrazine may be isolated as its free base or alternatively as its hydrochloride salt. This hydrazine may be reacted with ketone XXVIII to provide indole XXX by first treating with acetic acid in toluene followed by heating the resulting hydrazone at 60° C. in 4M HCl/dioxane. The nitrile functionality of indole XXX may be hydrolyzed to the carboxylic acid XXXI by first treating with methanolic HCl, followed by alkaline hydrolysis. XXXI is an example of compound Ia of the present invention.

Method F

It will be obvious to one skilled in the art that asymmetrically substituted compounds Ia may be sythesized as pure enantiomers or may be resolved into their pure enantiomers. For example, racemic Ia may be treated with KHMDS followed by pivaloyl chloride to form a mixed anhydride. The lithium salt of a chiral oxazolidinone may then be added to form a diastereotopic mixture of chiral imides XXXII and XXXIII, which are examples of compound Ib of the present invention. These two compounds may then be separated by chromatography or crystalization to provide the pure diastereomers. Each pure diastereomer may then be hydrolized independently with lithium hydroperoxide to generate the pure enantiomers XXXIV and XXXV which are examples of compound 1a of the present invention.

Method G

An indolepropanoic acid of the type Ia may be treated with 1,1'-carbonyldiimidazole in dichloromethane at room temperature to form an active ester. Subsequent treatment with an amine, acetamide, or sulfonamide of structure HNR$^9$R$^{10}$ and DMAP provides the desired amide, imide or acylsulfonamide which are examples of compound 1c of the present invention. Alternatively the coupling may be performed by reacting the lithium salt LiNR$^9$R$^{10}$ with the mixed anhydride described in Method F, thus providing examples of compound 1c of the present invention.

METHOD A

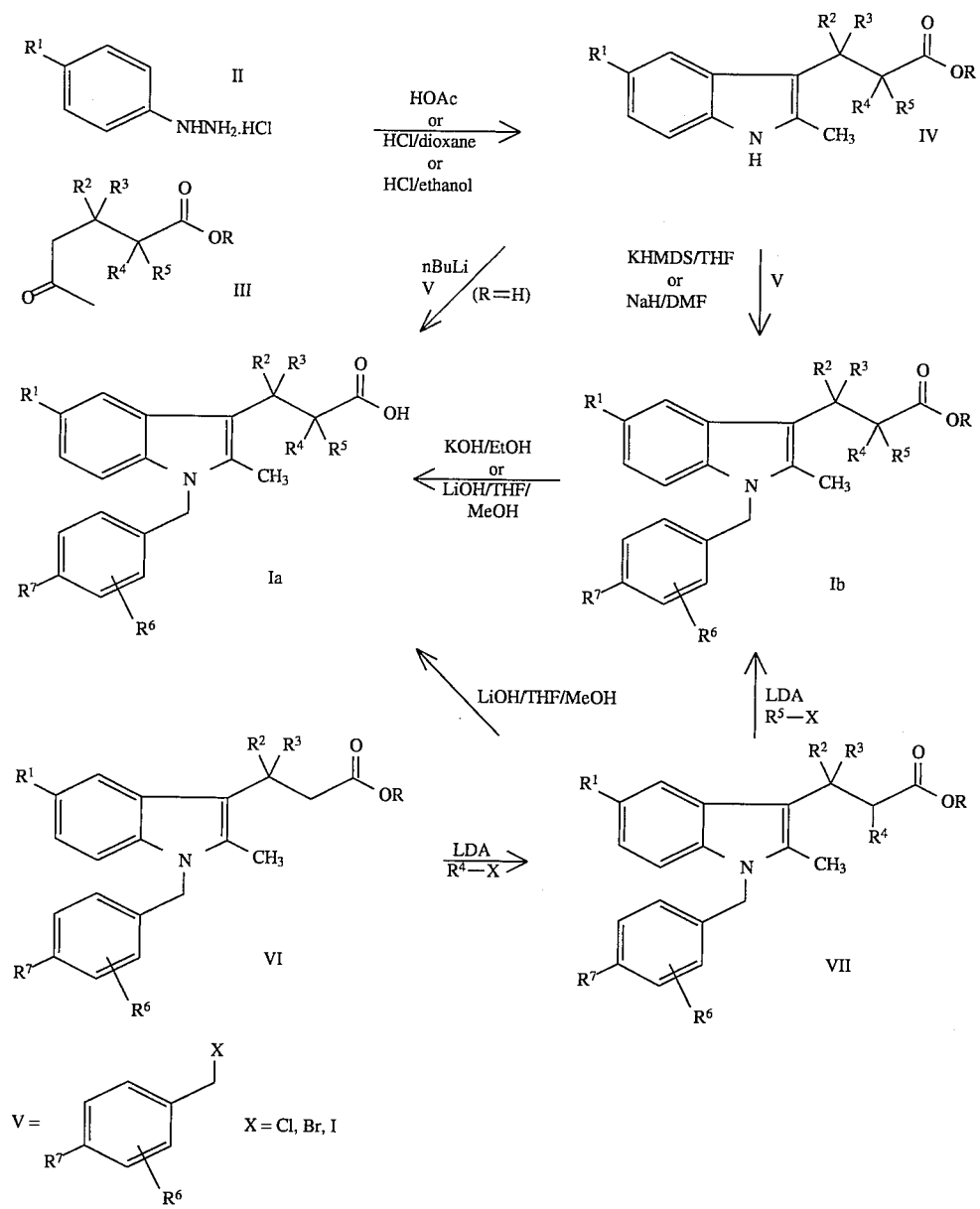

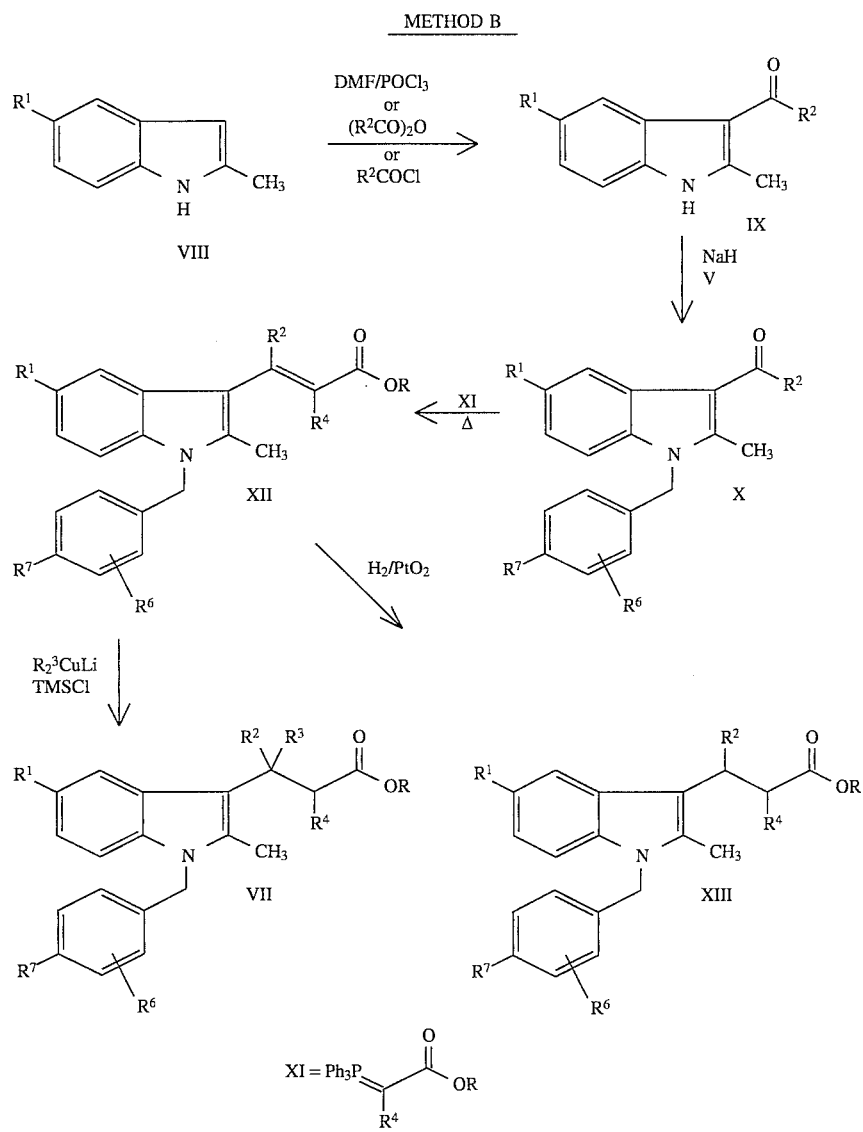
METHOD B
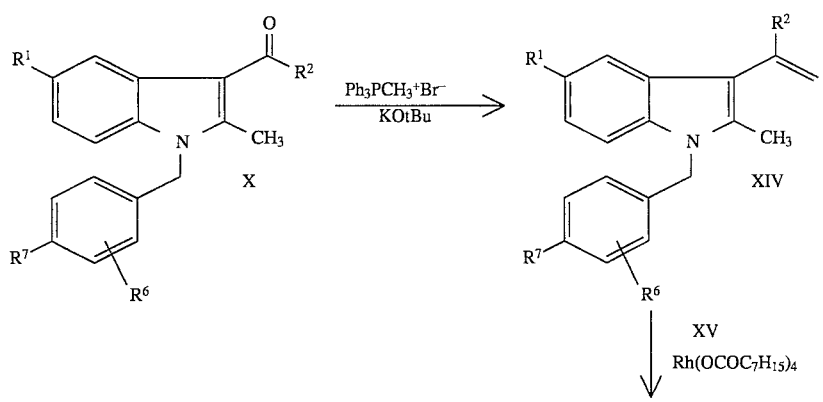
METHOD C

-continued
METHOD C
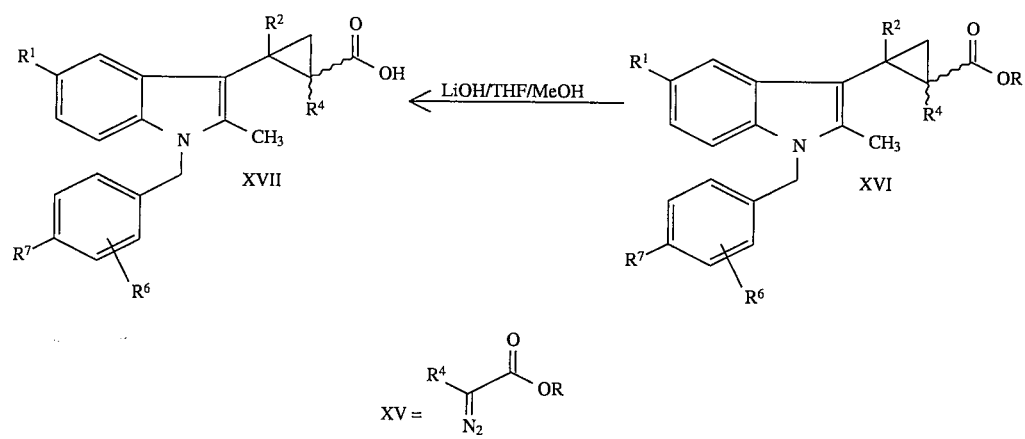
METHOD D
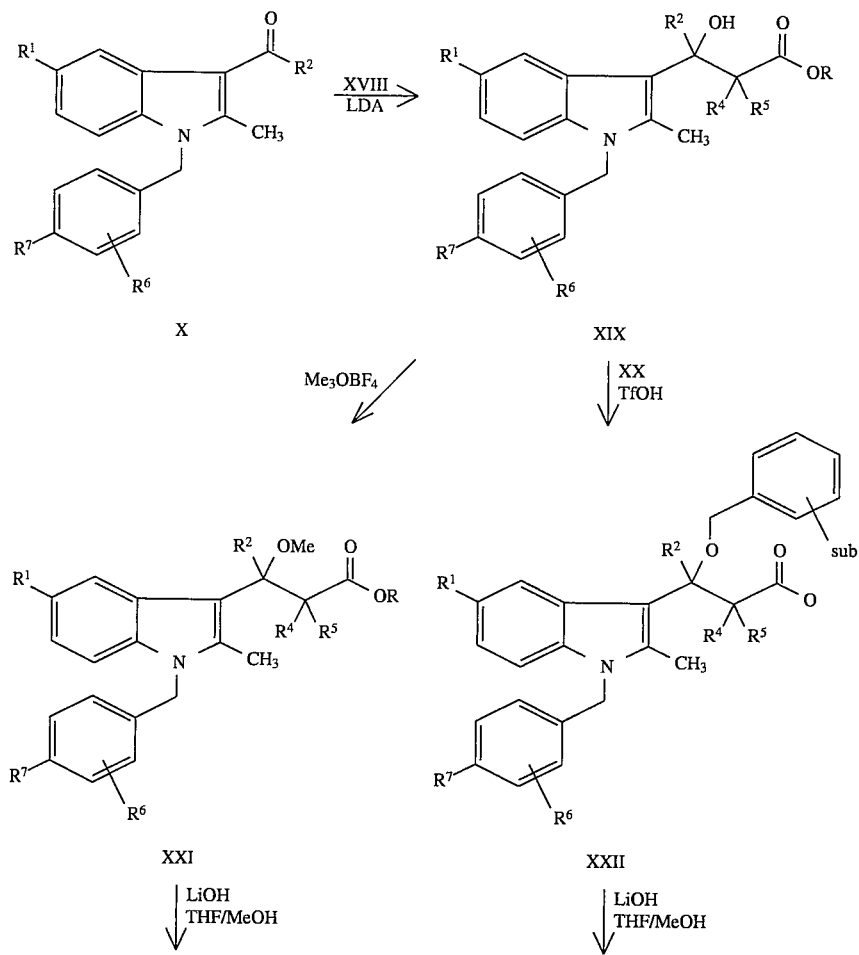

-continued
METHOD D
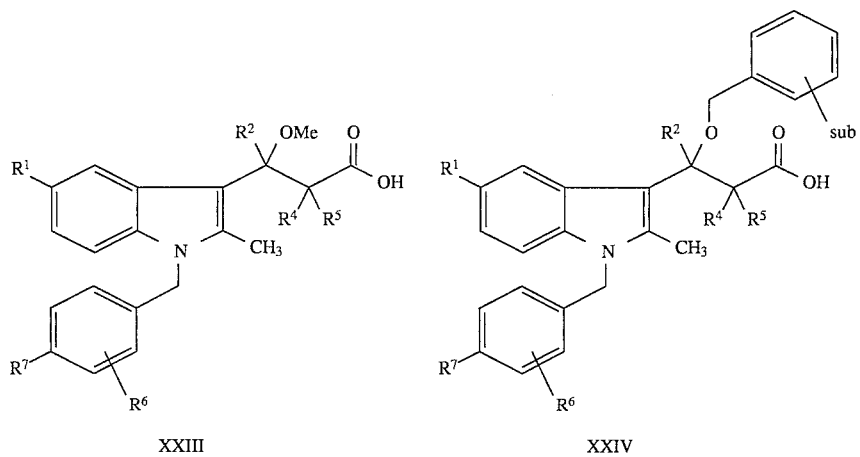
XXIII          XXIV
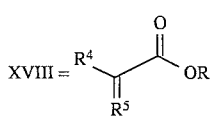     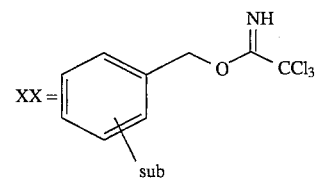
METHOD E
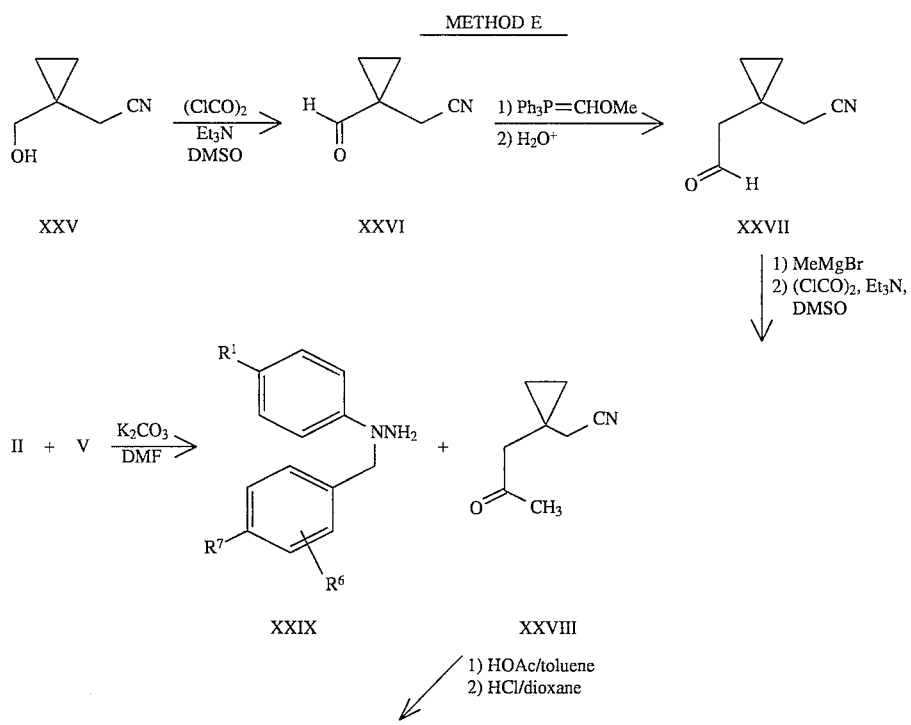

-continued
METHOD E
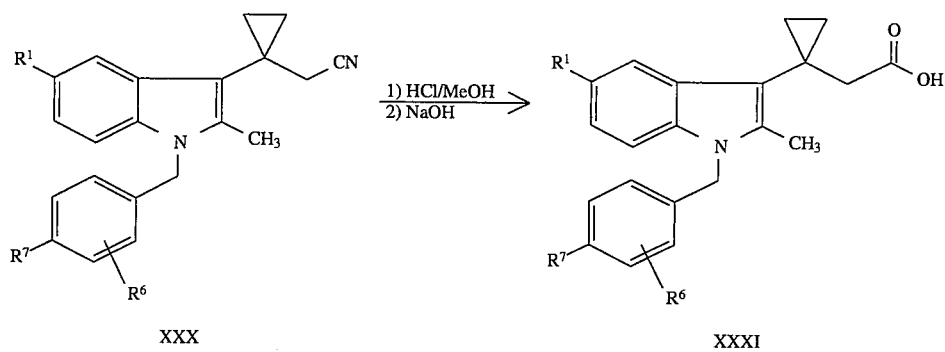
METHOD F
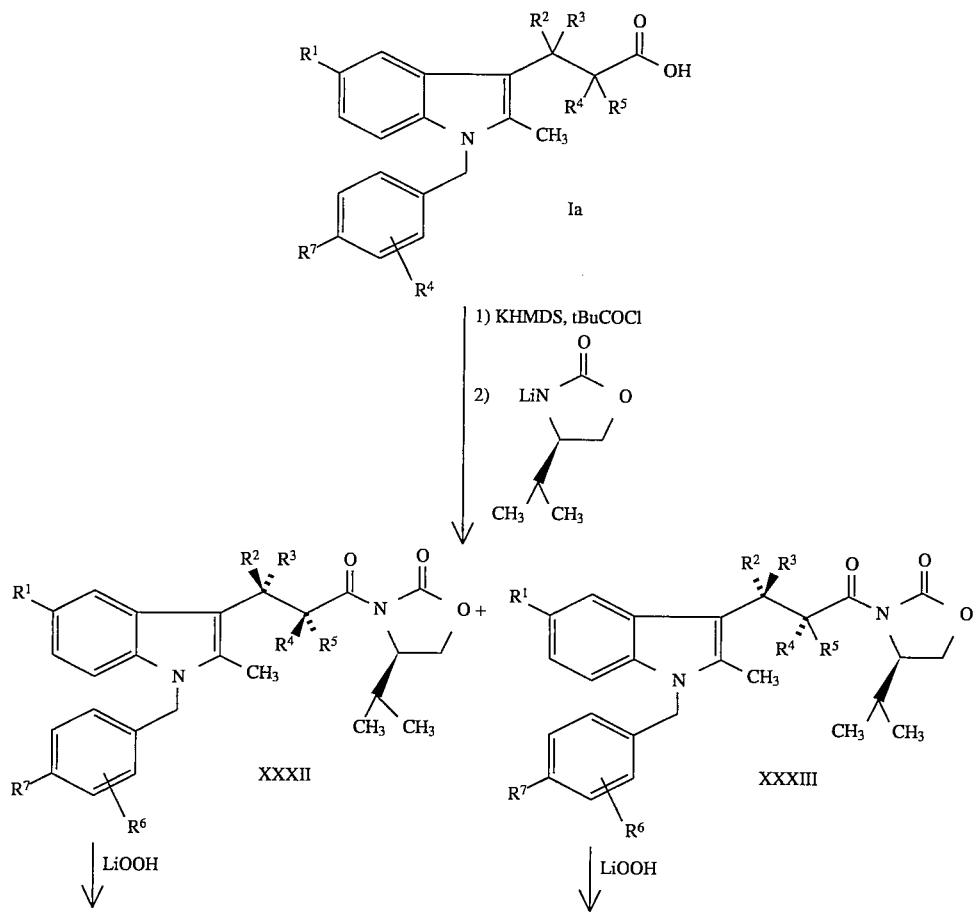

-continued
METHOD F

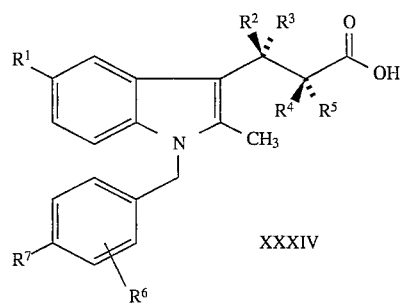

XXXIV

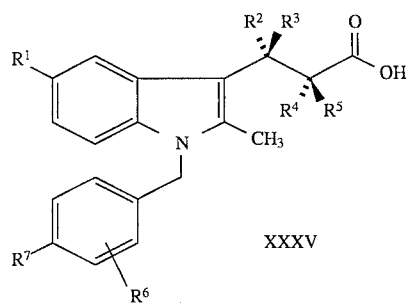

XXXV

METHOD G

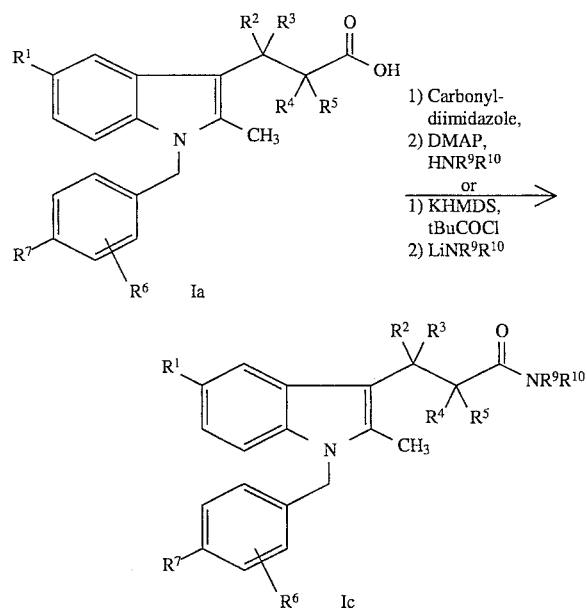

Representative Compounds

Table I illustrates compounds of Formula Ib, which are representative of the present invention:

TABLE I

| Example | Stereo | Q | R¹ | R² | R³ | R⁴ | R⁵ | R⁶ | R⁷ |
|---|---|---|---|---|---|---|---|---|---|
| 1 | N/A | H | MeO | H | H | H | H | H | Br |
| 2 | rac. | H | MeO | Me | H | H | H | H | Br |
| 3 | rac. | H | MeO | H | H | CH₂Ph | H | H | Br |
| 4 | N/A | H | MeO | H | H | Me | Me | H | Br |
| 5 | rac. | H | MeO | CF₃ | H | H | H | H | Br |
| 6 | trans, rac. | H | MeO | H | | —CH₂— | | H | Br |
| 7 | rac. | H | MeO | OH | H | Me | H | H | Br |
| 8 | N/A | H | MeO | —CH₂— | | H | H | H | Br |
| 9 | (+)-trans | H | MeO | H | | —CH₂— | H | H | Br |
| 10 | rac. | H | MeO | H | H | Me | H | H | Br |
| 11 | rac. | H | MeO | CF₃ | H | H | H | H | Cl |
| 12 | syn, rac. | H | MeO | H | Me | Me | H | H | Br |
| 13 | anti, rac. | H | MeO | H | Me | Me | H | H | Br |
| 14 | rac. | H | Br | Me | H | H | H | H | Br |
| 15 | (−) | H | MeO | Me | H | H | H | H | Br |
| 16 | (+) | H | MeO | Me | H | H | H | H | Br |
| 17 | (−)-trans | H | MeO | H | | —CH₂— | H | H | Br |
| 18 | N/A | H | Me | H | H | H | H | H | Br |
| 19 | N/A | H | Br | H | H | H | H | H | Br |
| 20 | N/A | H | Cl | H | H | H | H | H | Br |
| 21 | rac. | H | MeO | H | H | Me | H | H | Cl |
| 22 | N/A | Me | MeO | H | H | H | H | H | Br |

TABLE I-continued

| Example | Stereo | Q | $R^1$ | $R^2$ | $R^3$ | $R^4$ | $R^5$ | $R^6$ | $R^7$ |
|---|---|---|---|---|---|---|---|---|---|
| 23 | rac. | H | MeO | H | H | pMeS—PhCH$_2$ | H | H | Br |
| 24 | N/A | H | MeO | Me | Me | H | H | H | Br |
| 25 | anti, rac. | H | MeO | MeO | H | Me | H | H | Br |
| 26 | syn, rac. | H | MeO | MeO | H | Me | H | H | Br |
| 27 | rac. | Et | MeO | H | Me | H | H | H | Br |
| 28 | rac. | H | CH$_2$FO | Me | H | H | H | H | Br |
| 29 | rac. | H | MeO | Me | H | F | H | H | Br |
| 30 | rac. | H | MeO | Et | H | H | H | H | Br |
| 31 | rac. | H | MeO | H | H | Et | H | H | Br |
| 32 | rac. | H | MeO | Et | H | Me | H | H | Br |
| 33 | rac. | H | MeO | Me | H | Me | H | H | Br |
| 34 | anti, rac. | H | MeO | Me | H | Me | Me | H | Br |
| 35 | syn, rac. | H | MeO | Me | H | PhCH$_2$ | H | H | Br |
| 36 | anti, (+) | H | MeO | Me | H | PhCH$_2$ | H | H | Br |
| 37 | syn, (+) | H | MeO | Me | H | PhCH$_2$ | H | H | Br |
| 38 | anti, (−) | H | MeO | Me | H | PhCH$_2$ | H | H | Br |
| 39 | syn, (−) | H | MeO | Me | H | PhCH$_2$ | H | H | Br |
| 40 | rac. | H | MeO | Me | H | H | H | 2-F | Br |
| 41 | rac. | H | MeO | Me | H | H | H | 3-F | Br |
| 42 | rac. | H | MeO | H | H | pMeS(O)2—PhCH$_2$ | H | H | Br |
| 43 | rac. | H | MeO | H | H | PMeS(O)—PhCH$_2$ | H | H | Br |
| 44 | rac. | H | MeO | H | H | p-Ph—PhCH$_2$ | H | H | Br |
| 45 | rac. | H | MeO | —CH$_2$— | | Me | H | H | Br |
| 46 | rac. | H | MeO | Me | H | H | H | H | SMe |
| 47 | rac. | H | MeO | Me | H | H | H | H | SEt |
| 48 | rac. | H | MeO | Me | H | H | H | H | SCF$_2$H |
| 49 | rac. | H | MeO | H | H | PhCH$_2$ | Me | H | Br |
| 50 | rac. | H | Br | H | H | PhCH$_2$ | H | H | Br |
| 51 | rac. | H | MeO | H | | —CH$_2$CH$_2$CH$_2$— | H | H | Br |
| 52 | rac. | H | MeO | H | | —CH$_2$CH$_2$— | H | H | Br |
| 53 | N/A | H | MeO | H | H | —CH$_2$CH$_2$— | H | H | Br |
| 54 | rac. | H | MeO | H | H | Naphthyl-CH$_2$ | H | H | Br |
| 55 | rac. | H | MeO | SMe | H | H | H | H | Br |
| 56 | rac. | Me | MeO | Me | H | H | H | H | Br |
| 57 | rac. | Et | MeO | Me | H | H | H | H | Br |
| 58 | rac. | H | MeO | Me | H | H | H | H | I |

Table II illustrates compounds of Formula Ic, which are representative of the present invention:

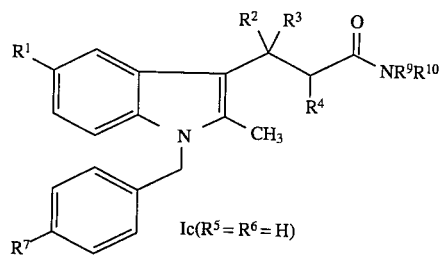

Ic($R^5 = R^6 = H$)

TABLE II

| Example | Stereo | $R^1$ | $R^2$ | $R^3$ | $R^4$ | $R^7$ | $R^9$ | $R^{10}$ |
|---|---|---|---|---|---|---|---|---|
| 59 | rac. | MeO | Me | H | H | Br | H | H |
| 60 | rac. | MeO | CF$_3$ | H | H | Br | H | S(O)$_2$Me |
| 61 | rac. | MeO | Me | H | H | Br | H | C(O)CH$_2$Ph |
| 62 | N/A | MeO | H | H | H | Br | H | 2-pyridyl |
| 63 | N/A | MeO | H | H | H | Br | Me | OMe |
| 64 | N/A | MeO | H | H | H | Br | H | H |
| 65 | N/A | MeO | H | H | H | Br | H | S(O)$_2$Me |
| 66 | N/A | MeO | H | H | H | Br | H | S(O)$_2$Ph |
| 67 | N/A | MeO | H | H | H | Br | H | S(O)$_2$CH$_2$Ph |
| 68 | N/A | MeO | H | H | H | Br | H | C(O)Me |
| 69 | N/A | MeO | H | H | H | Br | H | C(O)Ph |
| 70 | N/A | Cl | H | H | H | Br | H | H |
| 71 | N/A | MeO | H | H | H | Br | H | S(O)$_2$CH$_2$CH$_3$ |
| 72 | N/A | MeO | H | H | H | Br | H | S(O)$_2$n-Bu |
| 73 | N/A | MeO | H | H | H | Br | H | S(O)$_2$i-Pr |
| 74 | N/A | MeO | H | H | H | SMe | H | S(O)$_2$Me |
| 75 | rac | MeO | Me | H | H | Br | H | C(O)CF$_3$ |
| 76 | N/A | Br | H | H | H | Br | H | H |
| 77 | N/A | MeO | H | H | H | Br | H | (CH$_2$)$_3$NMe$_2$ |

Table III illustrates compounds of Formula I, which are representative of the present invention

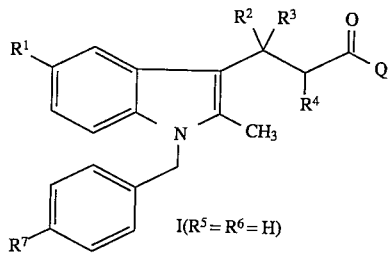

I($R^5 = R^6 = H$)

TABLE III

| Example | Stereo | R¹ | R² | R³ | R⁴ | R⁷ | Q |
|---|---|---|---|---|---|---|---|
| 78 | (R,R)/(S,R) | MeO | Me | H | H | Br | 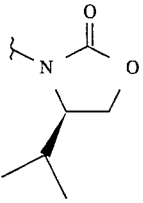 |
| 79 | rac. | MeO | Me | H | H | Br | 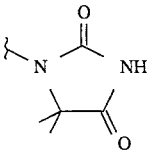 |
| 80 | rac. | MeO | Me | H | H | Br | 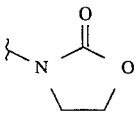 |
| 81 | rac. | MeO | Me | H | H | Br | 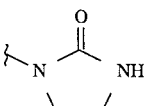 |
| 82 | N/A | MeO | H | H | H | Br | 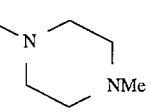 |
| 83 | rac. | MeO | Me | H | H | Br | 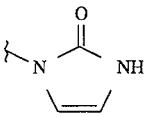 |
| 84 | rac. | MeO | H | H | H | Br | 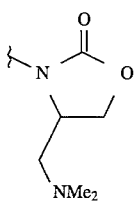 |

Assays for Determining Biological Activity

The compound of Formula I can be tested using the following assays to determine their cyclooxygenase-2 inhibiting activity.

Inhibition of Cyclooxygenase Activity

Compounds were tested as inhibitors of cyclooxygenase activity in whole cell cyclooxygenase assays. Both of these assays measured prostaglandin $E_2$ synthesis in response to arachidonic acid, using a radioimmunoassay. Cells used for these assays were human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition.

Assay

For cyclooxygenase assays, osteosarcoma cells are cultured in 1 mL of media in 24-well multidishes (Nunclon) until confluent (1–2×10⁵ cells/well). U-937 cells are grown in spinner flasks and resuspended to a final density of 1.5×10⁶ cells/mL in 24-well multidishes (Nunclon). Following washing and resuspension of osteosarcoma and U-937 cells in 1 mL of Hanks balanced salts solution (HBSS), 2 μL of a DMSO solution of test compound or DMSO vehicle is added, and samples gently mixed. All assays are performed in triplicate. Samples are then incubated for 5 or 15 minutes at 37° C., prior to the addition of arachidonic acid. Arachidonic acid (peroxide-free, Cayman Chemical) is prepared as a 10 mM stock solution in ethanol and further diluted 10-fold in HBSS. An aliquot of 10 μL of this diluted solution is added to the cells to give a final arachidonic acid concentration of 10 μM. Control samples are incubated with ethanol vehicle instead of arachidonic acid. Samples are again gently mixed and incubated for a further 10 min at 37° C. For osteosarcoma cells, reactions are then stopped by the addition of 100 μL of 1N HCl, with mixing and by the rapid removal of the solution from cell monolayers. For U-937 cells, reactions are stopped by the addition of 100 μL of 1N HCl, with mixing. Samples are then neutralized by the addition of 100 μL of 1N NaOH and $PGE_2$ levels measured by radioimmunoassay.

Rat Paw Edema Assay—Protocol

Male Sprague-Dawley rats (150–200 g) are fasted overnight and are given po either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 μl of 1% carrageenan solution in saline (FMC Corp, Maine) into the paw using an insulin syringe with a 25-gauge needle (i.e., 500 μg carrageenan per paw). Three hr later, the paw volume ($V_3$) is measured and the increases in paw volume ($V_3$–$V_0$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-Induced Gastrophathy in Rats

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of Hanks' balanced salt solution (HBSS). The red blood cells are incubated with 400 μCi of sodium $^{51}$chromate for 30 min at 37° C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 µCi) is injected per rat.

Protein-Losing Gastropathy in Squirrel Monkeys

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}$CrCl3 solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}$Cr (5 µCi/kg in 1 ml/kg phosphate buffer saline (PBS)) is administered 1 h after the last drug/vehicle dose, and feces collected for 24 h in a metabolism cage and assessed for excreted $^{51}$Cr by gamma-counting. Venous blood is sampled 1 h and 8 h after the last drug dose, and plasma concentrations of drag measured by RP-HPLC.

Representative Biological Data

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control.

Representative results for the inhibition of $PGE_2$ production and edema inhibition may be seen in Table IV. For comparison purposes, the Table also contains data for the conventional NSAID indomethacin and for the compound α-(1-p-chlorobenzyl-2-methyl-5-methoxy-3-indolyl)propionic acid (also known as MK-555). This latter compound is disclosed in British Patent Specification 957,990 (May 13, 1964) as having anti-inflammatory activity.

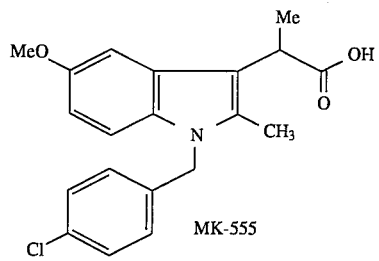

MK-555

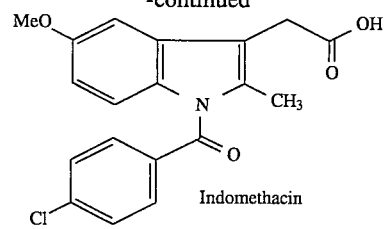

Indomethacin

TABLE IV

| Example | Cox-1 $IC_{50}$ (nM) | Cox-2 $IC_{50}$ (nM) | $ED_{30}$ (mg/kg) |
| --- | --- | --- | --- |
| 2 | >10,000 | 4 | 0.7 |
| 6 | >10,000 | 46 | 0.6 |
| MK-555 | 10,000 | 10 | 3.0 |
| Indomethacin | 10 | 10 | 0.9 |

The following abbreviations have the indicated meanings:
Ac=acetyl
Bn=benzyl
DMAP=4-(dimethylamino)pyridine
DMF=N,N-dimethylformamide
DMSO=dimethyl sulfoxide
$Et_3N$=triethylamine
HMPA=hexamethylphosphoric triamide
KHMDS=potassium hexamethyldisilazane
LDA=lithium diisopropylamide
LiHMDS=lithium hexamethyldisilazane
Ms=methanesulfonyl=mesyl
MsO=methanesulfonate=mesylate
NSAID=non-steroidal anti-inflammatory drug
PCC=pyridinium chlorochromate
Ph=phenyl
r.t.=room temperature
rac.=racemic
THF=tetrahydrofuran
TLC=thin layer chromatography Alkyl group abbreviations
Me=methyl
Et=ethyl Substituted benzyl, substituted phenyl and substituted pyridyl means that the aromatic ring carries 1 or 2 substituents selected from halo, methoxy, methylthio, trifluoromethyl, methyl or ethyl.

Halo includes F, Cl, Br, and I.

The invention will now be illustrated by the following non-limiting examples in which, unless stated otherwise: all operations were carried out at room or ambient temperature, that is, at a temperature in the range 18°–25° C.; evaporation of solvent wag carried out using a rotary evaporator under reduced pressure (600–4000 pascals: 4.5–30 mm Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only;

when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.; chemical symbols have their usual meanings; the following abbreviations have also been used b.p. (boiling point), m.p. (melting point), L (liter(s)), mL (milliliters), g (gram(s)), mg (milligrams(s)), mol (moles), mmol (millimoles).

EXAMPLE 1

3-[1-(p-Bromobenzyl)-5-methoxy-2-methylindol-3-yl]propanoic acid

Step 1:

3-(5-Methoxy-2-methylindol-3-yl)propanoic acid

A mixture of 5-methoxyphenylhydrazine hydrochloride (10.0 g, 57.3 mmol) and 5-ketohexanoic acid (7.54 g, 57.9 mmol) was suspended in 50 mL of acetic acid. The mixture was stirred 30 min at room temperature, 30 min at 60° C., and 16 h at 90° C. The resulting solution was cooled diluted with heptane and concentrated in vacuo. The residue was partitioned between water and ethyl acetate. The organic layer was washed with water and brine, dried over $MgSO_4$, filtered and evaporated. The resulting solid was swished from ether/hexanes to give 4.97 g of the title compound as a grey powder.

$^1$H NMR ($CD_3COCD_3$) δ7.13 (1H, d), 7.00 (1H, d), 6.64 (1H, dd), 3.78 (3H, s), 2.97 (2H, t), 2.56 (2H, t), 2.37 (3H, s).

Step 2:

3-[1-(p-Bromobenzyl)-5-methoxy-2-methylindol-3-yl]propanoic acid

To a cold (−78° C.) solution of the indole from Step 1 (877 mg, 4.04 mmol) in 40 mL of THF and 2.5 mL of HMPA was added n-BuLi (1.45M solution in hexanes, 5.6 mL, 8.12 mmol), giving a thick slurry. The mixture was warmed to 0° C., then cooled to −78° C. A solution of p-bromobenzyl bromide ( 1.18 g, 4.72 mmol) in 8 mL of THF was then added, and the mixture was warmed to room temperature. After 30 min, the reaction was poured into 1M HCl and extracted with ether. The organic layer was washed thrice with water, then with brine, dried over $MgSO_4$, filtered and evaporated. The residue was purified by flash chromatography (30% ethyl acetate/hexanes) to give 529 mg of the title compound as a crystaline solid.

$^1$H NMR ($CD_3COCD_3$) δ7.43 (2H, m), 7.16 (1H, d), 7.09 (1H, d), 6.90 (2H, m), 6.68 (1H, dd), 5.35 (2H, s), 3.79 (3H, s), 3.03 (2H, t), 2.59 (2H, t), 2.33 (3H, s).

EXAMPLE 2

3-[1-(p-Bromobenzyl)-5-methoxy-2-methylindol-3-yl]butanoic acid, sodium salt

Step 1:

3-Formyl-5-methoxy-2-methylindole

To 60 mL of DMF at 0° C. was added 10.1 mL of phosphorous oxychloride dropwise. The resulting solution was stirred 10 min at 0° C., then was treated dropwise with a solution of 5-methoxy-2-methylindole (16.2 g, 100 mmol) in 25 mL of DMF. The orange solution was wanned to 40° C. for 45 min, then cooled and quenched with ice. The mixture was then poured into 300 mL of ice water and treated with 100 mL of 10N NaOH. The resulting slurry was heated to reflux for 4 h, then cooled and filtered. The solid was rinsed with water and air-dried to give 18.7 g of the title compound.

$^1$H NMR ($CD_3COCD_3$) δ10.17 (1H, s), 7.71 (1H, d), 7.28 (1H, d), 6.79 (1H, dd), 3.80 (3H, s), 2.70 (3H, s).

Step 2:

1-(p-Bromobenzyl)-3-formyl-5-methoxy-2-methylindole

Sodium hydride (60% dispersion, 4.33 g, 108 mmol) was washed with hexane and suspended in 20 mL DMF. To a 0° C. solution of the indole from Step 1 (18.7 g, 98.9 mmol) and p-bromobenzyl bromide (25.6 g, 103 mmol) in 100 mL of DMF was added this NaH suspension, giving hydrogen evolution. After stirring 1.5 h, the resulting slurry was poured into 1.5 L of dilute aqueous $NH_4Cl$. The mixture was then extracted with 4:1 $CH_2Cl_2$/hexanes. The organic extract was washed with water and brine and filtered through cotton. Removal in vacuo of the majority of the solvent caused the product to crystalize, giving 24.9 g of the title compound. Recrystalization of the mother liquor provided an additional 7.05 g of the title compound.

$^1$H NMR ($CDCl_3$) δ10.18 (1H, s), 7.84 (1H, d), 7.45 (2H, m), 7.09 (1H, d), 6.88 (3H, m), 5.28 (2H, s), 3.90 (3H, s), 2.62 (3H, s).

Step 3:

Ethyl 3-[1-(p-bromobenzyl)-5-methoxy-2-methylindol-3-yl]propenoate

A mixture of the indole from Step 2 (8.46 g, 23.6 mmol) and (carbethoxymethylene)triphenylphosphorane (16.9 g, 48.6 mmol) was suspended in 25 mL of toluene and heated to reflux for 15 h. The solvent was removed in vacuo and the residue was purified by flash chromatography (25% ethyl acetate/hexanes) to provide 9.38 g of the title compound.

$^1$H NMR ($CD_3COCD_3$) δ7.97 (1H, d), 7.49 (2H, m), 7.39 (1H, d), 7.30 (1H, d), 7.00 (2H, m), 6.84 (1H, dd), 6.35 (1H, d), 5.47 (2H, s), 4.23 (2H. q), 3.88 (3H, s), 2.53 (3H, s), 1.30 (3H, t).

Step 4:

Ethyl 3-[1-(p-bromobenzyl)-5-methoxy-2-methylindol-3-yl]butanoate

To a 0° C. suspension of cuprous iodide (12.7 g, 67.0 mmol) in 150 mL ether was added $CH_3Li$ (1.4M in ether, 96 mL, 134 mmol). The solution was cooled to −78° C. and treated with TMSCl (8.5 mL, 67 mmol) and a solution of the unsaturated ester from Step 3 (6.79 g, 15.8 mmol) in 30 mL of THF. The yellow suspension was allowed to warm to room temperature and was stirred 2.5 h. The reaction mixture was poured into saturated $NH_4Cl$ and extracted with EtOAc. The organic extracts were washed with water and brine and dried over $Na_2SO_4$. Purification by flash chromatography (20% ethyl acetate/hexanes) provided 5.13 g of the title product as a crystaline solid.

$^1$H NMR ($CD_3COCD_3$) δ7.44 (2H, m), 7.15 (2H, m), 6.86 (2H, m), 6.69 (1H, dd), 5.34 (2H, s), 3.96 (2H, q), 3.82 (3H, s), 3.58 (1H, m), 2.79 (2H, m), 2.32 (3H, s), 1.46 (3H, d), 1.08 (3H, t).

Step 5:

3-[1-(p-Bromobenzyl)-5-methoxy-2-methylindol-3-yl]butanoic acid

To a suspension of the ester from Step 4 (5.13 g, 11.5 mmol) in 50 mL of EtOH was added 8N KOH (5 mL, 40 mmol) and 5 mL water. The mixture was heated to 60° C. for 1 h, then cooled and concentrated. The residue was partitioned between 1M HCl and EtOAc. The organic phase was washed with brine, dried over $MgSO_4$, filtered and evaporated. Crystallization from $CH_2Cl_2$/hexanes gave 3.59 g of the title compound.

$^1$H NMR ($CD_3COCD_3$) δ7.42 (2H, m), 7.25 (2H, m), 6.86 (2H, m), 6.69 (1H, dd), 5.34 (2H, s), 3.82 (3H, s), 3.58 (1H, m), 2.78 (2H, m), 2.34 (3H, s), 1.46 (3H, d).

Step 6:

Sodium 3-[1-(p-bromobenzyl)-5-methoxy-2-methylindol-3-yl]butanoate

A suspension of the acid from Step 5 (870 mg, 2.09 mmol) in 15 mL EtOH was treated with 1.00N NaOH (2.1 mL, 2.1 mmol), and stirred until the solid dissolved. The solution was concentrated to dryness, then dissolved in a minimum amount of water and freeze-dried to provide 914 mg of the title compound.

EXAMPLE 3

2-Benzyl-3-[1-(p-bromobenzyl)-5-methoxy-2-methylindol-3-yl]-propanoic acid

Step 1:

Methyl 3-[1-(p-bromobenzyl)-5-methoxy-2-methylindol-3-yl]propanoate

To a 0° C. solution of the acid from Example 1, Step 2 (900 mg, 2.24 mmol) in 10 mL of DMF was added iodomethane (0.18 mL, 2.89 mmol) followed by potassium carbonate (326 mg, 2.36 mmol). The mixture was warmed to room temperature, stirred 3 h, then poured into water and extracted with ether. The organic extracts were washed with water and brine, dried over $Na_2SO_4$ and evaporated to give 953 mg of the title compound.

$^1$H NMR ($CD_3COCD_3$) δ7.43 (2H, m), 7.15 (1H, d), 7.D6 (1H, d), 6.89 (2H, m), 6.70 (1H, dd), 5.33 (2H, s), 3.81 (3H, s), 3.57 (3H, s), 3.03 (2H, t), 2.60 (2H, t), 2.30 (3H, s).

Step 2:

Methyl 2-benzyl-3-[1-(p-bromobenzyl)-5-methoxy-2-methylindol-3-yl]propanoate To a −78° C. solution of the ester from Step 1 (130 mg, 0.312 mmol) in 5 mL of THF was added LDA (1.5M solution in cyclohexane, 0.25 mL, 0.38 mmol). The solution was warmed to 0° C., then cooled again to −78° C. Benzyl bromide (0.05 mL, 0.42 mmol) was added, the solution was allowed to warm to room temperature, and then was poured into water and extracted with ether. The organic extracts were washed with brine, dried over $Na_2SO_4$ and evaporated. Purification of the residue by flash chromatography (20% ethyl acetate/hexanes) provided 40 mg of the title compound.

$^1$H NMR ($CD_3COCD_3$) δ7.43 (2H, m), 7.25 (5H, m), 7.15 (1H, d), 6.85 (3H, m), 6.68 (1H, dd), 5.33 (2H, s), 3.77 (3H, s), 3.40 (3H, s), 3.05 (3H, m), 2.92 (2H, m), 2.25 (3H, s).

Step 3:

2-Benzyl-3-[1-(p-bromobenzyl)-5-methoxy-2-methylindol-3-yl]propanoic acid

To a room temperature solution of the methyl ester from Step 2 (40 mg, 0.08 mmol) in 3 mL THF and 5 mL MeOH was added 1 mL of 1M LiOH. The resulting solution was stirred 30 h at room temperature, then quenched with aqueous $NH_4Cl$ and concentrated in vacuo. The residue was partitioned between 1M HCl and EtOAc, washed with brine, dried over $Na_2SO_4$ and evaporated to give 30 mg of the title compound.

$^1$H NMR ($CD_3COCD_3$) δ7.40 (2H, m), 7.25 (5H, m), 7.13 (1H, d), 6.90 (1H, d), 6.84 (2H, m), 6.66 (1H, dd), 5.34 (2H, s), 3.75 (3H, s), 3.05 (3H, m), 2.90 (2H, m), 2.25 (3H, s).

EXAMPLE 4

3-[1-(p-bromobenzyl)-5-methoxy-2-methylindol-3-yl]-2,2-dimethylpropanoic acid Step 1:

Methyl 3-[1-(p-bromobenzyl)-5-methoxy-2-methylindol-3-yl]-2-methylpropanoate Using the method of Example 3, Step 2, but alkylating with iodomethane, 80 mg of the title compound was prepared.

$^1$H NMR ($CD_3COCD_3$) δ7.44 (2H, m), 7.15 (1H, d), 7.04 (1H, d), 6.88 (2H, m), 6.68 (1H, dd), 5.34 (2H, s), 3.79 (3H, s), 3.54 (3H, s), 3.07 (1H, m), 2.81 (2H, m), 2.28 (3H, s), 1.15 (3H, s).

Step 2:

Methyl 3-[1-(p-bromobenzyl)-5-methoxy-2-methylindol-3-yl]-2,2-dimethylpropanoate To a −78° C. solution of the ester from Step 1 (35 mg, 0.08 mmol) in 3 mL THF was added LDA (1.5M in cyclohexane, 0.1 mL, 0.15 mmol), and the solution was stirred for 30 min. A solution of iodomethane (0.1 mL, 1.6 mmol) in 1 mL HMPA was then added by syringe. The solution was stirred 15 min at −78° C., then warmed to 0° C. and quenched with saturated $NH_4Cl$. The mixture was partitioned between ether and water and the organic layer was washed with water and brine and dried over $MgSO_4$. The residue was purified by flash chromatography (15% ethyl acetate/hexanes) to provide 24 mg of the title compound.

$^1$H NMR ($CD_3COCD_3$) δ7.45 (2H, m), 7.16 (1H, d), 7.03 (1H, d), 6.88 (2H, m), 6.68 (1H, dd), 5.37 (2H, s), 3.78 (3H, s), 3.55 (3H, s), 2.98 (2H, s), 2.27 (3H, s), 1.24 (6H, s).

Step 3:

3-[1-(p-bromobenzyl)-5-methoxy-2-methylindol-3-yl]-2,2-dimethylpropanoic acid To a room temperature solution of the methyl ester from Step 2 (24 mg, 0.052 mmol) in 10 mL EtOH was added 1 mL of 4N KOH. The solution was heated to reflux for 22 h, then cooled and concentrated in vacuo. The residue was partitioned between 1M HCl and EtOAc. The organic layer was washed with brine, dried over $Na_2SO_4$ and evaporated to provide 23 mg of the title compound.

¹H NMR (CD₃COCD₃) δ7.43 (2H, m), 7.23 (2H, m), 7.03 (1H, d), 6.89 (2H, m), 6.68 (1H, dd), 5.36 (2H, s), 3.79 (3H, s), 3.04 (2H, s), 2.30 (3H, s), 1.22 (6H, s).

EXAMPLE 5

3-[1-(p-bromobenzyl)-5-methoxy-2-methylindol-3-yl]-4,4,4-trifluorobutanoic acid, sodium salt Step 1:

3-Trifluoroacetyl-5-methoxy-2-methylindole

To a 0° C. solution of 5-methoxy-2-methylindole (29.8 g, 185 mmol) in 80 mL of DMF was added trifluoroacetic anhydride (30 mL, 212 mmol) over 30 min. The resulting slurry was then poured into 1.2 L of water. The precipitate was filtered and dried under vacuum at 80° C. overnight to give 24.6 g of the title compound.

¹H NMR (CD₃COCD₃) δ7.58 (1H, d), 7.38 (1H, d), 6.88 (1H, dd), 3.84 (3H, s), 2.75(3H, s).

Step 2:

Ethyl 3-(5-methoxy-2-methylindol-3-yl)-4,4,4-trifluoro-2-butenoate

A suspension of the indole from Step 1 (18.3 g, 71.4 mmol) and carbethoxy-methylenetriphenylphosphorane (49.7 g, 142.8 mmol) in 100 mL of toluene was pressurized to 900 psi nitrogen in a stainless steel, high pressure Parr reactor and was heated to 120° C. for 39 h. The reaction mixture was cooled, concentrated and purified by flash chromatography (30% ethyl acetate/hexanes) to give 23 g of the title compound as a mixture of E- and Z- isomers.

E-isomer: ¹H NMR (CD₃COCD₃) δ7.23 (1H, d), 6.84 (1H, q), 6.80 (1H, d), 6.72 (1H, dd), 3.98 (2H, q), 3.76 (3H, s), 2.30 (3H, s), 0.96 (3H, t).

Z-isomer: ¹H NMR (CD₃COCD₃) δ7.25 (1H, d), 6.92 (1H, d), 6.76 (1H, dd), 6.44 (1H, s), 4.28 (2H, q), 3.79 (3H, s), 2.43 (3H, s), 1.31 (3t).

Step 3:

Ethyl 3-(5-methoxy-2-methylindol-3-yl)-4,4,4-trifluorobutanoate

A solution of the indole from Step 2 (23 g, 70 mmol) in 200 mL EtOH was treated with 60 psi hydrogen over 5% palladium on carbon (2.3 g) in a Parr shaker for 18 h. The mixture was filtered through celite and evaporated to give 23 g of the title compound.

¹H NMR (CD₃COCD₃) δ7.20 (1H, d), 7.16 (1H, d), 6.70 (1H, dd), 4.22 (1H, m), 4.00 (2H, m), 3.80 (3H, s), 3.15 (2H, m), 2.45 (3H, s), 1.07 (3H, t).

Step 4:

Ethyl 3-[1-(p-bromobenzyl)-5-methoxy-2-methylindol-3-yl]-4,4,4-trifluorobutanoate To a −78° C. solution of the indole from Step 3 (3.1 g, 9.4 mmol) in 65 mL of THF was added KHMDS (0.6M toluene solution, 18.8 mL, 11.3 mmol) dropwise. The solution was warmed to 0° C., then cooled to −78° C. A solution of p-bromobenzyl bromide (3.0 g, 12.2 mmol) was then added, and the solution was allowed to warm to room temperature. The solution was then poured into 1M HCl and extracted with ether. The organic extracts were washed with brine, dried over MgSO₄ and evaporated. The residue was purified by flash chromatography (20% ethyl acetate/hexanes) to provide 3.0 g of the title compound.

¹H NMR (CD₃COCD₃) δ7.44 (2H, m), 7.23 (1H, d), 7.14 (1H, d), 6.89 (2H, m), 6.74 (1H, dd), 5.42 (2H, s), 4.30 (1H, m), 3.98 (2H, m), 3.82 (3H, s), 3.20 (2H, m), 2.40 (3H, s), 1.06 (3H, t).

Step 5:

3-[1-(p-bromobenzyl)-5-methoxy-2-methylindol-3-yl]-4,4,4-trifluorobutanoic acid To a mixture of the ester from Step 4 (4.6 g, 9.2 mmol) in 45 mL of EtOH was added 10N NaOH (2.3 mL, 23 mmol) and the mixture was heated to reflux for 2 h. The mixture was cooled and concentrated and the residue was partitioned between ether and 1M HCl. The organic layer was dried over MgSO₄ and evaporated to give a white solid. This material was swished with 10% ether/hexane to give 4.0 g of the title compound.

¹H NMR (CD₃COCD₃) δ7.45 (2H, m), 7.25 (1H, d), 7.17 (1H, d), 6.90 (2H, m), 6.74 (1H, dd), 5.43 (2H, s), 4.32 (1H, m), 3.82 (3H, s), 3.20 (2H, m), 2.41 (3H, s).

Step 6:

3-[1-(p-Bromobenzyl)-5-methoxy-2-methylindol-3-yl]-4,4,4-trifluorobutanoic acid, sodium salt Using the method of Example 2, Step 6, the title compound was obtained.

EXAMPLE 6 trans-2-[1-(p-Bromobenzyl)-5-methoxy-2-methylindol-3-yl]-cyclo-propanecarboxylic acid, sodium salt Step 1:

1-(p-Bromobenzyl)-5-methoxy-2-methyl-3-vinylindole

To a 0° C. suspension of methyltriphenylphosphonium bromide (12.8 g, 35.9 mmol) in 130 mL THF was added potassium tert-butoxide (1.75M THF solution, 20.5 mL, 35.9 mmol). The resulting yellow mixture was stirred 45 min at room temperature, then cooled to −78° C. A solution of the indole from Example 2, Step 2 (9.33 g, 26.0 mmol) in 70 mL of CH₂Cl₂ was added via cannula, and the mixture was allowed to warm to room temperature. After stirring 1.5 h, the reaction was quenched with saturated NH₄Cl and concentrated. The residue was partitioned between water and CH₂Cl₂. The organic layer was washed with brine, filtered through cotton and evaporated. Purification by flash chromatography (40% ethyl acetate/hexanes) provided 9.06 g of the title compound.

¹H NMR (CD₃COCD₃) δ7.48 (2H, m), 7.35 (1H, d), 7.24 (1H, d), 6.95 (3H, m), 6.76 (1H, dd), 5.60 (1H, dd), 5.42 (2H, s), 5.14 (1H, dd), 3.82 (3H, s), 2.39 (3H, s).

Step 2:

Ethyl 2-[1-(p-bromobenzyl)-5-methoxy-2-methylindol-3-yl]cyclopropanecarboxylate To a room temperature solution of the indole from Step 1 (3.91 g, 11.0 mmol) in 20 mL toluene was added rhodium (II) octanoate dimer (109 mg, 0.14 mmol), and the solution was cooled to 0° C. A solution of ethyl diazoacetate (3.0 mL, 28.5 mmol) in 13 mL toluene was then added via syringe pump at 1.2 mL/hr. Fresh catalyst was then added along with an additional 1 mL ethyl diazoacetate in toluene over 2.5 h. The crude reaction mixture was applied directly to a silica gel column and eluted with 1% to 2.5% ethyl acetate/toluene. 1.1 g of the trans isomer of the title compound was thus obtained, followed by 1.2 g of the cis isomer of the title compound.

cis isomer:

$^1$H NMR (CD$_3$COCD$_3$) δ7.43 (2H, m), 7.12 (2H, m), 6.86 (2H, m), 6.68 (1H, dd), 5.34 (2H, s), 4.20 (2H, q), 3.80 (3H, s), 2.44 (1H, m), 2.32 (3H, s), 2.17 (1H, m), 1.54 (2H, m), 1.26 (3H, t).

trans isomer:

$^1$H NMR (CD$_3$COCD$_3$) δ7.46 (2H, m), 7.18 (1H, d), 7.06 (1H, d), 6.94 (2H, m), 6.70 (1H, dd), 5.34 (2H, s), 4.22 (2H, q), 3.80 (3H, s), 2.35 (3H, s), 2.31 (1H, m ), 1.84 (1H, m), 1.55 (1H, m), 1.30 (1H, m), 1.27 (3H, t).

Step 3:

trans-2-[1-(p-Bromobenzyl)-5-methoxy-2-methylindol-3-yl]-cyclopropanecarboxylic acid To a solution of the trans isomer of the cyclopropane from Step 2 (2.39 g, 5.40 mmol) in 15 mL THF and 25 mL MeOH was added 10 mL of 1M LiOH. The mixture was stirred at room temperature for 16 h, then concentrated in vacuo. The residue was partitioned between 1M HCl and CH$_2$C$_2$. The organic phase was washed with brine, filtered through cotton and evaporated. Crystalization from CH$_2$C$_2$/hexanes provided 1.55 g of the title compound.

$^1$H NMR (CD$_3$COCD$_3$) δ7.46 (2H, m), 7.18 (1H, d), 7.09 (1H, d), 6.94 (2H, m), 6.71 (1H, dd), 5.34 (2H, s), 3.80 (3H, s), 2.39 (3H, s), 2.34 (1H, m), 1.84 (1H, m), 1.55 (1H, m), 1.31 (2H, m).

Step 4:

trans-2-[1-(p-Bromobenzyl)-5-methoxy-2-methylindol-3-yl]-cyclopropanecarboxylic acid, sodium salt Using the method of Example 2, Step 6, the title compound was obtained.

EXAMPLE 7

3-[1-(p-Bromobenzyl)-5-methoxy-2-methylindol-3-yl]-3-hydroxy-2-methyl propanoic acid, sodium salt Step 1:

Methyl 3-[1-(p-bromobenzyl)-5-methoxy-2-methylindol-3-yl]-3-hydroxy-2-methyl propanoate To a –78° C. solution of diisopropylamine (672 mg, 6.64 mmol) in 20 mL THF was added n-BuLi (1.45M in hexanes, 4.6 mL, 6.7 mmol). The solution was warmed to 0° C., then cooled again to –78° C. Methyl propanoate (0.64 mL, 6.6 mmol) was then added and the solution was allowed to warm to 0° C., then cooled again to –78° C. A solution of the aldehyde from Example 2, Step 2 (1.42 g, 3.96 mmol) in 14 mL THF was then added via cannula. The resulting solution was stirred 40 min, then was allowed to warm slowly to room temperature and stirred 1.5 h. The reaction was quenched with saturated NH$_4$Cl and diluted with ether. The organic phase was washed with 1M HCl and brine, then dried over Na$_2$SO$_4$ and evaporated to give 2.06 g of the title compound as a 3:2 mixture of anti- and syn-isomers.

syn-isomer:

$^1$H NMR (CD$_3$COCD$_3$) δ7.45 (2H, m), 7.28 (1H, d), 7.19 (1H, d), 6.93 (2H, m), 6.71 (1H, dd), 5.38 (2H, s), 5.08 (1H, dd), 4.16 (1H, d), 3.79 (3H, s), 3.70 (3H, s), 3.13 (1H, m), 2.38 (3H, s), 0.87 (3H, d).

anti-isomer:

$^1$H NMR (CD$_3$COCD$_3$) δ7.45 (2H, m), 7.26 (1H, d), 7.14 (1H, d), 6.86 (2H, m), 6.69 (1H, dd), 5.35 (2H, s), 5.09 (1H, dd), 4.21 (1H, d), 3.79 (3H, s), 3.38 (3H, s), 3.12 (1H, m), 2.31 (3H, s), 1.36 (3H, d).

Step 2:

3-[1-(p-Bromobenzyl)-5-methoxy-2-methylindol-3-yl]-3-hydroxy-2-methyl propanoic acid To a room temperature solution of the aldol adduct from Step 1 (247 mg, 0.55 mmol) in 4 mL THF and 25 mL methanol was added 3 mL of 1M LiOH solution. Stirred 62 h at room temperature, then concentrated in vacuo. The residue was partitioned between 1M HCl and CH$_2$Cl$_2$. The organic phase was washed with brine and filtered through cotton. Purification by flash chromatography on silicic acid (35% ethyl acetate/hexanes) provided 78 mg of the title compound as a 2:1 mixture of syn and anti isomers.

syn-isomer:

$^1$H NMR (CD$_3$COCD$_3$) δ7.45 (2H, m), 7.21 (2H, m), 6.90 (2H, m), 6.73 (1H, dd), 5.42 (2H, s), 4.66 (1H, m), 3.78 (3H, s), 2.39 (1H, m), 2.38 (3H, s), 0.89 (3H, d).

Step 3:

3-[1-(p-Bromobenzyl)-5-methoxy-2-methylindol-3-yl]-3-hydroxy-2-methylpropanoic acid, sodium salt Using the method of Example 2, Step 6, the title compound was obtained.

EXAMPLE 8

[1-(1-(p-Bromobenzyl)-5-methoxy-2-methylindol-3-yl)-cyclopropyl]acetic acid, sodium salt Step 1:

(1-Formylcyclopropane)acetonitrile

To a room temperature suspension of PCC (32.3 g, 150 mmol) and celite (35 g) in 200 mL CH$_2$Cl$_2$ was added (1-hydroxymethylcyclopropane)acetonitrile (Eur. Pat. 604, 114, Example 1, Step 7, Case 18907, 11.1 g, 100 mmol) in 20 mL CH$_2$Cl$_2$ over 15 min. The mixture was stirred 4 h, then filtered through a 1:1 mixture of celite and silica gel, washing with 50% ether/CH$_2$Cl$_2$. The filtrate was concentrated in vacuo, then dissolved in CH$_2$C$_2$ and dried over MgSO$_4$, filtered and evaporated to give 10.6 g of the title compound.

$^1$H NMR (CD$_3$COCD$_3$) δ8.65 (1H, s), 2.75 (2H, s), 1.2–1.5 (4H, m).

Step 2:

[1-(2-Oxoethyl)cyclopropyl]acetonitrile

To a –5° C. suspension of (methoxymethyl)triphenylphosphonium chloride (28.3 g, 82.5 mmol) in 160 mL THF was added potassium t-butoxide (1.75M solution in THF, 46 mL, 81 mmol). The deep orange mixture was stirred 15 min, then transferred dropwise via cannula into a –5° C. solution of the aldehyde from Step 1 (6.0 g, 55 mmol) in 115 mL THF. After stirring 2 h at 0° C., the reaction mixture was partitioned between 1M HCl and ethyl acetate. The organic layer was washed with brine, dried over MgSO$_4$, filtered and evaporated. The residue was filtered through a plug of silica gel with 20% ethyl acetate/hexanes to provide the intermediate enol ether. This material was dissolved in 110 mL of methanol and treated with 30 mL of 4N HCl and refluxed overnight. The cooled reaction mixture was partitioned between water and ethyl acetate. The organic layer was washed with brine, dried over $MgSO_4$, filtered and evaporated. Purification by flash chromatography (15% ethyl acetate/hexanes) provided 3.0 g of the title compound.

$^1$H NMR ($CD_3COCD_3$) δ9.8 (1H, s), 2.65 (2H, s), 2.55 (2H, d), 0.7–0.5 (4H, m).
Step 3:

[1-(2-Hydroxypropyl)cyclopropyl]acetonitrile

To a –5° C. solution of the aldehyde from Step 2 (3.00 g, 24.4 mmol) in 65 mL of THF was added methyl magnesium chloride (3.0M solution in THF, 9.5 mL, 29 mmol) and the reaction was stirred 2 h at 0° C. The reaction was quenched with 1M HCl and extracted with ethyl acetate. The organic extracts were washed with saturated $NaHCO_3$ and brine and dried over $MgSO_4$. Purification by flash chromatography (30% ethyl acetate/hexanes) provided 2.46 g of the title product.

$^1$H NMR ($CD_3COCD_3$) δ4.0–3.75 (1H, m), 3.6 (1H, d), 2.85–2.40 (2H, m), 1.25–1.75 (2H, m), 1.10 (3H, d), 0.6–0.4 (4H, m).
Step 4:

[1-(2-Oxopropyl)cyclopropyl]acetonitrile

To a –78° C. solution of oxalyl chloride (0.70 mL, 8.0 mmol) in 40 mL of $CH_2Cl_2$ was added DMSO (0.62 mL, 8.7 mmol) and the resulting solution was stirred for 10 min. A solution of the alcohol from Step 3 (2.46 g, 17.7 mmol) in 5 mL $CH_2Cl_2$ was then added, and the mixture stirred 1 h at –78° C. Triethylamine (4.2 mL, 30 mmol) was then added, and the solution was allowed to warm to room temperature and stirred overnight. The reaction mixture was then partitioned between 1M HCl and $CH_2Cl_2$, and the organic layer was washed with saturated $NaHCO_3$ and brine, dried over $MgSO_4$ and evaporated. Purification of the residue by flash chromatography (25% ethyl acetate/hexanes) provided 927 mg of the title compound.

$^1$H NMR ($CD_3COCD_3$) δ2.7–2.5 (4H, m), 2.1 (3H, s), 0.6–0.4 (4H, m).
Step 5:

N-(p-Bromobenzyl)-N-(4-methoxyphenyl)hydrazine hydrochloride

A mixture of 4-methoxyphenylhydrazine hydrochloride (459 g, 2.63 mol), p-bromobenzyl bromide (715 g, 2.86 mol) and milled potassium carbonate (771 g, 5.58 mol) was suspended in 2 L DMF at 0° C. with overhead stirring. The ice bath was removed and the mixture was stirred for 4 h, then diluted with 15 L of ice water. The mixture was stirred vigourously for 1 h, then the aqueous layer was decanted from the gummy solid. The solid was washed with 2×4 L of water, then was dissolved in 2.5 L toluene and dried over $Na_2SO_4$. The mixture was filtered, and the filtrate was cooled in an ice bath and treated with a stream of HCl gas for 1 h with vigourous stirring. The precipitate was filtered and washed with 3×0.5 L of cold toluene and dried under a stream of nitrogen to give 682 g of the title compound.

$^1$H NMR ($CD_3SOCD_3$) δ10.5 (2H, br, s), 7.50 (2H, m), 7.23 (4H, m), 6.90 (2H, m), 4.52 (2H, s), 3.68 (3H, s).

Step 6:

[1-(1-(p-Bromobenzyl)-5-methoxy-2-methylindol-3-yl)-cyclopropyl]acetonitrile

To a 0° C. mixture of the ketone from Step 4 (920 mg, 6.71 mmol) and the hydrazine from Step 5 (2.15 g, 7.0 mmol) in 35 mL toluene was added acetic acid (0.97 mL, 17 mmol). The mixture was warmed to room temperature and stirred 1 h, then concentrated to dryness. The residue was dissolved in toluene and heptane and concentrated again and the process repeated until there was no more acetic acid remaining. The residue was then dissolved in 30 mL dioxane and treated with HCl (4M solution in dioxane, 4 mL, 16 mmol). The mixture was heated to 60° C. for 1.5 h, then cooled and partitioned between water and ethyl acetate. The organic phase was washed with saturated $NaHCO_3$ and brine, dried over $MgSO_4$ and evaporated. Purification by flash chromatography (15% ethyl acetate/hexanes) provided 2.32 g of the title compound.

$^1$H NMR ($CD_3COCD_3$) δ7.50–6.65 (7H, m), 5.35 (2H, s), 3.8 (3H, s), 2.75 (2H, s), 2.45 (3H, s), 1.1–0.85 (4H, m).
Step 7:

Methyl [1-(1-(p-bromobenzyl)-5-methoxy-2-methylindol-3-yl)cyclopropyl]acetate

To a –5° C. suspension of the nitrile from Step 6 (1.59 g, 3.88 mmol) in 15 mL methanol was added HCl gas to give a saturated solution. The mixture was then heated to reflux overnight, cooled and poured into ice water. The mixture was adjusted to pH 10 with 2.0N NaOH, and then extracted with ethyl acetate. The organic extracts were washed with saturated $NaHCO_3$ and brine, dried over $MgSO_4$ and evaporated. Purification by flash chromatography (15% ethyl acetate/hexanes) provided 1.63 g of the title compound.

$^1$H NMR ($CD_3COCD_3$) δ7.50–6.65 (7H, m), 5.30 (2H, s), 3.85 (3H, s), 3.45 (3H, s), 2.50 (2H, s), 2.30 (2H, s), 1.1–0.85 (4H, s).
Step 8:

[1-(1-(p-Bromobenzyl)-5-methoxy-2-methylindol-3-yl)cyclopropyl]acetic acid

To the methyl ester from Step 7 (1.63 g, 3.68 mmol) in 20 mL of methanol was added 5 mL of 2N NaOH, and the mixture was heated to reflux for 2 h then cooled. The reaction mixture was partitioned between ethyl acetate and 1M HCl. The organic layer was washed with brine, dried over $MgSO_4$ and evaporated to give a solid. This material was swished twice in 15% ether/hexane to provide 1.23 g of the title compound.

$^1$H NMR ($CD_3COCD_3$) δ10.3–10.2 (1H, br), 7.50–6.65 (7H, Ar), 5.30 (2H, s), 3.80 (3H, s), 2.55 (2H, s), 2.35 (3H, s), 1.1–0.85 (4H, m).
Step 9:

[1-(1-(p-Bromobenzyl)-5-methoxy-2-methylindol-3-yl)cyclopropyl]acetic acid, sodium salt Using the method of Example 2, Step 6, the title compound was obtained.

EXAMPLE 9 trans-(+)-2-[1-(p-Bromobenzyl)-5-methoxy-2-methylindol-3-yl]cyclopropanecarboxylic acid, sodium salt Step 1:

(4R)-3-[trans-2-(1-(p-Bromobenzyl)-5-methoxy-2-methylindol-3-yl)cyclopropanecarbonyl]-4-isopropyl-2-oxazolidinone To a 0° C. solution of the acid from Example 6 Step 3 (2.22 g, 5.35 mmol) in 60 mL THF was added KHMDS (0.5M toluene solution, 11 mL, 5.5 mmol) followed by pivaloyl chloride (0.72 mL, 5.84 mmol). The mixture was stirred for 20 min, then cooled to −78° C. In a separate flask, a −78° C. solution of (4R)-(+)-4-isopropyl-2-oxazolidinone (767 mg, 5.94 mmol) in 30 mL THF was treated with n-BuLi (1.4M solution in hexanes, 4.3 mL, 6.0 mmol). The mixture was stirred 10 min, then transferred via cannula to the −78° C. mixed anhydride solution. The mixture was allowed to warm to 0° C., stirred 20 min, then quenched with saturated $NH_4Cl$ and concentrated in vacuo. The residue was partitioned between ether and 1M HCl. The organic layer was washed with brine, dried over $MgSO_4$, filtered and evaporated. Purification by flash chromatography (4% ethyl acetate/toluene) provided 1.07 g of one diastereomer of the title compound, and 1.05 g of the other diastereomer of the title compound.

high $R_f$ diastereomer:
$^1$H NMR ($CD_3COCD_3$) δ 7.45 (2H, m), 7.17 (1H, d), 7.06 (1H, d), 6.94 (2H, m), 6.68 (1H, dd), 5.34 (2H, s), 4.59 (1H, m), 4.45 (1H, m), 4.37 (1H, dd), 3.77 (3H, s), 3.58 (1H, m), 2.45 (1H, m), 2.38 (3H, s), 2.35 (1H, m), 1.70 (1H, m), 1.39 (1H, m), 0.94 (3H, d), 0.90 (3H, d).

low $R_f$ diastereomer:
$^1$H NMR ($CD_3COCD_3$) δ 7.45 (2H, m), 7.18 (1H, d), 7.08 (1H, d), 6.95 (2H, m), 6.69 (1H, dd), 5.35 (2H, s), 4.58 (1H, m), 4.48 (1H, m), 4.36 (1H, dd), 3.80 (3H, s), 3.66 (1H, m), 2.40 (2H, m), 2.38 (3H, s), 1.70 (1H, m), 1.41 (1H, m), 0.98 (6H, m).

Step 2:

trans-(+)-2-[1-(p-Bromobenzyl)-5-methoxy-2-methylindol-3-yl]cyclopropanecarboxylic acid To a −10° C. solution of the low $R_f$ diastereomerically pure imide from Step 1 (967 mg, 1.84 mmol) in 20 mL THF was added 2 mL of 30% $H_2O_2$ and 3 mL of 1M LiOH. Stirred 2.5 h at 0° C., then quenched with 1M $Na_2S_2O_3$ and concentrated. The residue was partitioned between 1M HCl and ethyl acetate. The organic phase was washed with brine and dried over $Na_2SO_4$. Purification by flash chromatography on silicic acid (30% ethyl acetate/hexanes) followed by recrystallization provided 490 mg of the title compound in enantiomerically pure form.

$[α]_D$ +85° (c 0.93, $CH_2Cl_2$); $^1$H NMR ($CD_3COCD_3$) δ 7.46 (2H, m), 7.18 (1H, d), 7.09 (1H, d), 6.94 (2H, m), 6.71 (1H, dd), 5.34 (2H, s), 3.80 (3H, s), 2.39 (3H, s), 2.34 (1H, m), 1.84 (1H, m), 1.55 (1H, m), 1.31 (2H, m).

Step 3:

trans-(+)-2-[1-(p-Bromobenzyl)-5-methoxy-2-methylindol-3-yl]cyclopropanecarboxylic acid, sodium salt Using the method of Example 2, Step 6, the title compound was obtained.

EXAMPLE 10

3-[1-(p-Bromobenzyl)-5-methoxy-2-methylindol-3-yl]-2-methylpropanoic acid and sodium salt Using the method of Example 3, the title compounds were obtained.

$^1$H NMR ($CD_3COCD_3$) δ 7.44 (2H, m), 7.15 (1H, d), 7.08 (1H, d), 6.88 (2H, m), 6.68 (1H, dd), 5.34 (2H, s), 3.80 (3H, s), 3.13 (1H, m), 2.80 (2H, m), 2.30 (3H, s), 1.15 (3H, d).

EXAMPLE 11

3-[1-(p-Chlorobenzyl)-5-methoxy-2-methylindol-3-yl]-4,4,4-trifluorobutanoic acid and sodium salt Using the method of Example 5, the title compounds were obtained.

$^1$H NMR ($CD_3COCD_3$) δ 7.29 (2H, m), 7.25 (1H, d), 7.15 (1H, d), 6.94 (2H, m), 6.74 (1H, dd), 5.43 (2H, s), 4.30 (1H, m), 3.82 (3H, s), 3.20 (2H, m), 2.39 (3H, s).

EXAMPLE 12 syn-3-[1-(p-Bromobenzyl)-5-methoxy-2-methylindol-3-yl]-2-methylbutanoic acid

Using the method of Example 2, the title compound was obtained.

$^1$H NMR ($CD_3COCD_3$) δ 7.44 (2H, m), 7.19 (1H, d), 7.11 (1H, d), 6.90 (2H, m), 6.70 (1H, dd), 5.38 (2H, s), 3.80 (3H, s), 3.18 (1H, m), 2.95 (1H, m), 2.33 (3H, s), 1.43 (3H, d), 0.93 (3H, d).

EXAMPLE 13 anti-3-[1-(p-Bromobenzyl)-5-methoxy-2-methylindol-3-yl]-2-methylbutanoic acid and sodium salt Using the method of Example 2, but using (carbethoxyethylidene)triphenylphosphorane in the Wittig reaction, the title compounds were obtained.

$^1$H NMR ($CD_3COCD_3$) δ 7.40 (2H, m), 7.15 (1H, d), 7.12 (1H, d), 6.84 (2H, m), 6.65 (1H, dd), 5.34 (2H, s), 3.80 (3H, s), 3.25 (1H, m), 3.02 (1H, m), 2.30 (3H, s), 1.46 (3H, d), 1.30 (3H, d).

EXAMPLE 14

3-[5-Bromo-1-(p-bromobenzyl)-2-methylindol-3-yl]butanoic acid and sodium salt

Using the method of Example 8, the title compounds were obtained.

$^1$H NMR ($CD_3COCD_3$) δ 7.83 (1H, d), 7.44 (2H, m), 7.26 (1H, d), 7.13 (1H, dd), 6.88 (2H, m), 5.90 (2H, s), 3.58 (1H, m), 2.79 (2H, m), 2.37 (3H, s), 1.45 (3H, d).

EXAMPLE 15

(−)-3-[1-(p-Bromobenzyl)-5-methoxy-2-methylindol-3-yl]-butanoic acid and sodium salt Using the method of Example 9, the compound of Example 2 was resolved and the title compounds were obtained.

[α]$_D$−37° (c 0.91, CH$_2$Cl$_2$); 1H NMR (CD$_3$COCD$_3$) δ7.42 (2H, m), 7.25 (2H, m), 6.86 (2H, m), 6.69 (1H, dd), 5.34 (2H, s), 3.82 (3H, s), 3.58 (1H, m), 2.78 (2H, m), 2.34 (3H, s), 1.46 (3H, d).

EXAMPLE 16

(+)-3-[1-(p-Bromobenzyl)-5-methoxy-2-methylindol-3-yl]-butanoic acid and sodium salt Using the method of Example 9, the compound of Example 2 was resolved and the title compounds were obtained.

[α]$_D$+37° (c 0.1.02, CH$_2$Cl$_2$); $^1$H NMR (CD$_3$COCD$_3$) δ7.42 (2H, m), 7.25 (2H, m), 6.86 (2H, m), 6.69 (1H, dd), 5.34 (2H, s), 3.82 (3H, s), 3.58 (1H, m), 2.78 (2H, m), 2.34 (3H, s), 1.46 (3H, d).

EXAMPLE 17 trans-(−)-2-[1-(p-Bromobenzyl)-5-methoxy-2-methylindol-3-yl]cyclopropanecarboxylic acid and sodium salt The high R$_f$ diastereomer from Example 9 Step 1 was convened by the method of Example 9 Steps 2 and 3 into the title compounds.

[α]$_D$−99° (c 0.90, CH$_2$Cl$_2$); $^1$H NMR (CD$_3$COCD$_3$) δ7.46 (2H,m), 7.18 (1H, d), 7.09 (1H, d), 6.94 (2H, m), 6.71 (1H, dd), 5.34 (2H, s), 3.80 (3H, s), 2.39 (3H, s), 2.34 (1H, m), 1.84 (1H, m), 1.55 (1H, m), 1.31 (2H, m).

EXAMPLE 18

3-[1-(p-Bromobenzyl)-2,5-dimetbylindol-3-yl)propanoic acid

Using the method of Example 1, the title compound was obtained.

$^1$H NMR (CD$_3$COCD$_3$) δ7.45 (2H, m), 7.37 (1H, s), 7.15 (1H, d), 6.90 (3H, m), 5.37 (2H, s), 3.05 (2H, t), 2.60 (2H, t), 2.40 (3H, s), 2.35 (3H, s).

EXAMPLE 19

3-[5-Bromo-1-(p-bromobenzyl)-2-methylindol-3-yl)propanoic acid

Using the method of Example 1, the title compound was obtained.

m.p. 169°–170° C.

EXAMPLE 20

3-[1-(p-Bromobenzyl)-5-chloro-2-methylindol-3-yl)propanoic acid

Using the method of Example 1, the title compound was obtained.

m.p. 154°–155° C.

EXAMPLE 21

3-[1-(p-Chlorobenzyl)-5-methoxy-2-methylindol-3-yl)-2-methylpropanoic acid

Using the method of Example 3, but alkylating with iodomethane, the title compound was obtained.

$^1$H NMR (CD$_3$COCD$_3$) δ7.30–6.65 (7H, m), 5.35 (2H, s), 3.80 (3H, s), 3.1 (1H, m), 2.80 (2H, m), 2.30 (3H, s), 1.15 (3H, d).

EXAMPLE 22

Methyl 3-[1-(p-bromobenzyl)-5-methoxy-2-methylindol-3-yl)propanoate

To a solution of the compound from Example 1 (75 mg, 0.19 mmol) in 10 mL EtOAc was added ethereal diazomethane solution until a yellow colour persisted. The solution was concentrated in vacuo and crystalized from ether/hexanes to provide 67 mg of the title compound.

$^1$H NMR (CD$_3$COCD$_3$) δ7.43 (2H, m), 7.16 (1H,d), 7.05 (1H, d), 6.88 (2H, m), 6.68 (1H, dd), 5.32 (2H, s), 3.79 (3H, s), 3.55 (3H, s), 3.03 (2H, t), 2.60 (2H, t), 2.30 (3H, s).

EXAMPLE 23

3-[1-(p-Bromobenzyl)-5-methoxy-2-methylindol-3-yl]-2-(p-methylthiobenzyl)propanoic acid Using the method of Example 3, but alkylating with p-methyl-thiobenzyl iodide, the title compound was obtained.

$^1$H NMR (CD$_3$COCD$_3$) δ7.41 (2H, m), 7.21 (4H, s), 7.14 (1H, d), 6.90 (1H, d), 6.86 (2H, m), 6.68 (1H, dd), 5.34 (2H, s), 3.76 (3H, s), 3.15–2.80 (5H, m), 2.48 (3H, s), 2.28 (3H, s).

EXAMPLE 24

3-[1-(p-Bromobenzyl)-5-methoxy-2-methylindol-3-yl)-3-methylbutanoic acid

Step 1:

3,3-Dimethyl-5-oxohexanoic acid

A mixture of 1,4,4-trimethylcyclopentene (*J. Chem. Soc., Perkin* 2, 1979, 1535) (2.5 g, 22.7 mmol), sodium periodate (19.4 g, 90.7 mmol), and ruthenium(IV) oxide (66 mg, 0.50 mmol) was suspended in 140 mL of CCl$_4$/CH$_3$CN/H$_2$O (2:2:3) and stirred vigorously for 1 h. The mixture was then diluted with water and extracted three times with CH$_2$Cl$_2$. The combined organic phases were dried over MgSO$_4$ and evaporated. Purification of the residue provided the title compound as a colorless liquid.

Step 2:

3-[1-(p-Bromobenzyl)-5-methoxy-2-methylindol-3-yl)-3-methylbutanoic acid

Using the acid from Step 1 and the method of Example 1, the title compound was obtained.

$^1$H NMR (CD$_3$COCD$_3$) δ7.36 (2H, m), 7.29 (1H, m), 7.02 (1H, d), 6.73 (3H, m), 5.20 (2H, s), 3.82 (3H, s), 3.54 (3H, s), 2.90 (2H, s), 2.40 (3H, s), 1.68 (6H, s).

Examples 25 to 58 may be prepared analogously to the examples listed above.

Examples 59 to 73 and Examples 78 to 82 were prepared according to Method G.

Examples 74 to 77 and Examples 83 to 84 may be prepared according to Method G.

What is claimed is:

1. A compound of formula I

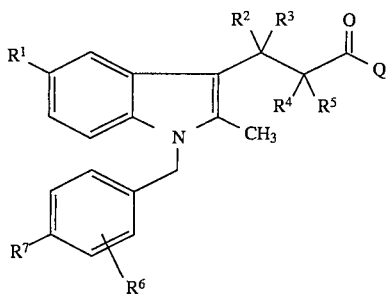

or a pharmaceutically acceptable salt thereof, wherein:

Q is
(a) —OR or
(b) —$NR^9R^{10}$;

R is
(a) —H or
(b) —$C_{1-4}$ alkyl;

$R^1$ is
(a) —$OCH_3$,
(b) —$OCH_2F$,
(c) —$OCHF_2$,
(d) F, Cl, Br or I, or
(e) methyl or ethyl;

$R^2$, $R^3$, $R^4$ and $R^5$ are independently
(a) —H,
(b) —F,
(c) methyl or ethyl,
(d) —$CF_3$, $CF_2H$, or $CFH_2$,
(e) —OH, $OR^8$, $SR^8$, $S(O)R^8$, or $S(O)_2R^8$,
(f) mono- or di-substituted benzyl, wherein the substituent is selected from
(1) hydrogen,
(1) $CF_3$,
(3) CN,
(4) F, Cl, Br or I,
(5) $C_{1-6}$alkyl,
(6) $SR^8$, $S(O)R^8$, or $S(O)_2R^8$,
(g) naphthylmethyl,
or $R^2$ together with $R^3$ form an oxo group;
or $R^4$ together with $R^5$ form an oxo group;
or $R^2$ and $R^3$ are joined so that together with the carbon atom to which they are attached there is formed a saturated monocyclic hydrocarbon ring of 3, 4, 5, 6 or 7 members;
or $R^2$ and $R^4$ are joined so that together with the carbon atoms to which they are attached there is formed a saturated monocyclic hydrocarbon ring of 3, 4, 5, 6 or 7 members;
or $R^2$ and $R^5$ are joined so that together with the carbon atoms to which they are attached there is formed a saturated monocyclic hydrocarbon ring of 3, 4, 5, 6 or 7 members;
or $R^3$ and $R^4$ are joined so that together with the carbon atoms to which they are attached there is formed a saturated monocyclic hydrocarbon ring of 3, 4, 5, 6 or 7 members;
or $R^3$ and $R^5$ are joined so that together with the carbon atoms to which they are attached there is formed a saturated monocyclic hydrocarbon ring of 3, 4, 5, 6 or 7 members;
or $R^4$ and $R^5$ are joined so that together with the carbon atom to which they are attached there is formed a saturated monocyclic hydrocarbon ring of 3, 4, 5, 6 or 7 members;

$R^6$ is H or F;

$R^7$ is
(a) Br, Cl or I,
(b) SMe, SEt, or $SCF_2H$;

$R^8$ is methyl, ethyl or mono- or di-substituted benzyl, wherein the substituent is selected from
(1) hydrogen,
(2) $CF_3$,
(3) CN,
(4) F, Cl, Br or I,
(5) $C_{1-6}$alkyl;

$R^9$ and $R^{10}$ are independently
(a) —H,
(b) —$C_{1-3}$ alkyl,
(c) —OR,
(d) —$C(O)R^{11}$,
(e) —$S(O)_2R^{12}$,
(f) mono-substituted $C_{2-4}$ alkyl wherein the substituent is selected from
(1) hydroxy,
(2) amino,
(3) methylamino, and
(4) dimethylamino,
provided that said substituent is located on a carbon of $C_{2-4}$ alkyl other than the one attached to the nitrogen of —$NR^9R^{10}$,
(g) phenyl, benzyl or pyridyl optionally mono- or di-substituted, the substituents being selected from the group consisting of
(1) hydrogen,
(2) $CF_3$,
(3) CN,
(4) F, Cl, Br or I,
(5) $C_{1-6}$alkyl;
or $R^9$ and $R^{10}$ are joined so that together with the nitrogen atom to which they are attached there is formed a saturated or unsaturated monocyclic ring of 3, 4, 5, 6, or 7 members, optionally containing one or two additional heteroatoms, said heteroatoms independently selected from N, O and S, said ring optionally containing one or two carbonyl or sulfonyl groups;

$R^{11}$ is
(a) H,
(b) —$C_{1-4}$ alkyl,
(c) —$CF_3$,
(d) phenyl or benzyl optionally mono- or di-substituted, the substituents being selected from the group consisting of
(1) hydrogen,
(2) $CF_3$,
(3) CN,
(4) F, Cl, Br or I,
(5) $C_{1-6}$alkyl;

$R^{12}$ is
(a) —$C_{1-4}$ alkyl,
(b) —$CF_3$,
(c) phenyl or benzyl optionally mono- or di-substituted, the substituents being selected from the group consisting of
(1) hydrogen,
(2) $CF_3$,
(3) CN,
(4) F, Cl, Br or I,
(5) $C_{1-6}$alkyl;

with the proviso that when Q is OR and $R^1$ is OMe and $R^2$, $R^3$, $R^4$, $R^5$ and $R^6$ are simultaneously hydrogen, $R^7$ is other than Cl.

2. A compound according to claim 1 wherein
Q is
- (a) —OR or
- (b) —NR$^9$R$^{10}$;

R is
- (a) —H or
- (b) —C$_{1-4}$ alkyl;

R$^1$ is
- (a) —OCH$_3$,
- (b) —OCH$_2$F,
- (c) —OCHF$_2$,
- (d) F, Cl, Br or I, or
- (e) methyl or ethyl;

R$^2$ and R$^3$ are independently
- (a) —H,
- (b) —F,
- (c) methyl or ethyl,
- (d) —CF$_3$,
- (e) —OH or SR$^8$, R$^4$ and R$^5$ are independently
- (a) —H,
- (b) methyl or ethyl,
- (c) —OH or SR$^8$,
- (d) mono- or di-substituted benzyl, wherein the substituent is selected from
  - (1) hydrogen,
  - (1) CF$_3$,
  - (3) CN,
  - (4) F, Cl, Br or I,
  - (5) C$_{1-6}$alkyl,
  - (6) SR$^8$, S(O)R$^8$, or S(O)$_2$R$^8$,
- (e) naphthylmethyl, or R$^2$ and R$^3$ are joined so that together with the carbon atom to which they are attached there is formed a saturated monocyclic hydrocarbon ring of 3, 4, 5, 6 or 7 members;
or R$^3$ and R$^4$ are joined so that together with the carbon atoms to which they are attached there is formed a saturated monocyclic hydrocarbon ring of 3, 4, 5, 6 or 7 members;

R$^6$ is H or F;

R$^7$ is
- (a) Br, Cl or I,
- (b) SMe, SEt, or SCF$_2$H;

R$^8$ is methyl, ethyl or mono- or di-substituted benzyl, wherein the substituent is selected from
- (1) hydrogen,
- (2) CF$_3$,
- (3) CN,
- (4) F, Cl, Br or I,
- (5) C$_{1-6}$alkyl;

R$^9$ is hydrogen or methyl;

R$^{10}$ is
- (a) —H,
- (b) —C$_{1-3}$ alkyl,
- (c) —OR,
- (d) —C(O)R$^{11}$,
- (e) —S(O)$_2$R$^{12}$,
- (f) mono-substituted C$_{2-4}$ alkyl wherein the substituent is selected from
  - (1) hydroxy,
  - (2) amino,
  - (3) methylamino, and
  - (4) dimethylamino,
provided that said substituent is located on a carbon of C$_{2-4}$ alkyl other than the one attached to the nitrogen of —NR$^9$R$^{10}$,
- (g) phenyl, benzyl or pyridyl optionally mono- or di-substituted, the substituents being selected from the group consisting of
  - (1) hydrogen,
  - (2) CF$_3$,
  - (3) CN,
  - (4) F, Cl, Br or I,
  - (5) C$_{1-4}$alkyl;

R$^{11}$ is
- (a) H,
- (b) —C$_{1-4}$ alkyl,
- (c) —CF$_3$,
- (d) phenyl or benzyl optionally mono- or di-substituted, the substituents being selected from the group consisting of
  - (1) hydrogen,
  - (2) CF$_3$,
  - (3) CN,
  - (4) F, Cl, Br or I,
  - (5) C$_{1-6}$alkyl;

R$^{12}$ is
- (a) —C$_{1-4}$ alkyl,
- (b) —CF$_3$,
- (c) phenyl or benzyl optionally mono- or di-substituted, the substituents being selected from the group consisting of
  - (1) hydrogen,
  - (2) CF$_3$,
  - (3) CN,
  - (4) F, Cl, Br or I,
  - (5) C$_{1-6}$alkyl.

3. A compound according to claim 2 wherein
Q is
- (a) —OR or
- (b) —NR$^9$R$^{10}$;

R is
- (a) —H or
- (b) —C$_{1-4}$ alkyl;

R$^1$ is
- (a) —OCH$_3$,
- (b) —OCH$_2$F,
- (c) —OCHF$_2$,
- (d) F, Cl, Br or I,
- (e) methyl or ethyl;

R$^2$ and R$^3$ are independently
- (a) —H,
- (b) —F,
- (c) methyl or ethyl,
- (d) —CF$_3$,
- (e) —OH or SR$_8$, R$^4$ is
- (a) —H,
- (b) methyl or ethyl,
- (c) —OH or SR$^8$,
- (f) mono- or di-substituted benzyl, wherein the substituent is selected from
  - (1) hydrogen,
  - (2) CF$_3$,
  - (3) CN,
  - (4) F, Cl, Br or I,
  - (5) C$_{1-4}$alkyl,
  - (6) SR$^8$, S(O)R$^8$, or S(O)$_2$R$^8$,
- (g) naphthylmethyl, or R$^2$ and R$^3$ are joined so that together with the carbon atom to which they are attached there is formed a saturated monocyclic hydrocarbon ring of 3, 4, 5, 6 or 7 members;

or $R^3$ and $R^4$ are joined so that together with the carbon atoms to which they are attached there is formed a saturated monocyclic hydrocarbon ring of 3, 4, 5, 6 or 7 members;

$R^5$ is H or methyl;

$R^6$ is H or F;

$R^7$ is
- (a) Br, Cl or I,
- (b) SMe, SEt, or $SCF_2H$;

$R^8$ is methyl, ethyl or mono- or di-substituted benzyl, wherein the substituent is selected from
- (1) hydrogen,
- (2) $CF_3$,
- (3) CN,
- (4) F, Cl, Br or I,
- (5) $C_{1-4}$alkyl;

$R^9$ is hydrogen or methyl;

$R^{10}$ is
- (a) —H,
- (b) —$C_{1-3}$ alkyl,
- (c) —OR,
- (d) —C(O)$R^{11}$,
- (e) —S(O)$_2R^{12}$,
- (f) phenyl, benzyl or pyridyl optionally mono- or di-substituted, the substituents being selected from the group consisting of
  - (1) hydrogen,
  - (2) $CF_3$,
  - (3) CN,
  - (4) F, Cl, Br or I,
  - (5) $C_{1-4}$alkyl;

$R^{11}$ is
- (a) H,
- (b) —$C_{1-4}$ alkyl,
- (c) —$CF_3$,
- (d) phenyl or benzyl optionally mono- or di-substituted, the substituents being selected from the group consisting of
  - (1) hydrogen,
  - (2) $CF_3$,
  - (3) CN,
  - (4) F, Cl, Br or I,
  - (5) $C_{1-4}$alkyl;

$R^{12}$ is
- (a) —$C_{1-4}$ alkyl,
- (b) —$CF_3$,
- (c) phenyl or benzyl optionally mono- or di-substituted, the substituents being selected from the group consisting of
  - (1) hydrogen,
  - (2) $CF_3$,
  - (3) CN,
  - (4) F, Cl, Br or I,
  - (5) $C_{1-4}$alkyl.

4. A compound according to claim 3 wherein

Q is
- (a) —OR or
- (b) —$NR^9R^{10}$;

R is
- (a) —H or
- (b) —$C_{1-3}$ alkyl;

$R^1$ is
- (a) —$OCH_3$,
- (b) —$OCH_2F$,
- (c) —$OCHF_2$,
- (d) F, Cl, Br or I,
- (e) methyl or ethyl;

$R^2$ and $R^3$ are independently
- (a) —H,
- (b) —F,
- (c) methyl or ethyl,
- (d) —$CF_3$,
- (e) —OH or $SR^8$, $R^4$ is
- (a) —H,
- (b) methyl or ethyl,
- (c) —OH or $SR^8$,
- (f) mono- or di-substituted benzyl, wherein the substituent is selected from
  - (1) hydrogen,
  - (2) $CF_3$,
  - (3) CN,
  - (4) F, Cl, Br or I,
  - (5) $C_{1-3}$alkyl,
  - (6) $SR^8$, $S(O)R^8$, or $S(O)_2R^8$,
- (g) naphthylmethyl, or $R^2$ and $R^3$ are joined so that together with the carbon atom to which they are attached there is formed a saturated monocyclic hydrocarbon ring of 3, 4, 5, 6 or 7 members;

or $R^3$ and $R^4$ are joined so that together with the carbon atoms to which they are attached there is formed a saturated monocyclic hydrocarbon ring of 3, 4, 5, 6 or 7 members;

$R^5$ is H or methyl;

$R^6$ is H or F;

$R^7$ is
- (a) Br, Cl or I,
- (b) SMe, SEt, or $SCF_2H$;

$R^8$ is methyl, ethyl or mono- or di-substituted benzyl, wherein the substituent is selected from
- (1) hydrogen,
- (2) $CF_3$,
- (3) CN,
- (4) F, Cl, Br or I,
- (5) $C_{1-3}$alkyl;

$R^9$ is hydrogen or methyl;

$R^{10}$ is
- (a) —H,
- (b) —$C_{1-3}$ alkyl,
- (c) —OR,
- (d) —C(O)$R^{11}$,
- (e) —S(O)$_2R^{12}$, $R^{11}$ is
- (a) H,
- (a) —$C_{1-3}$ alkyl,
- (a) —$CF_3$,
- (d) phenyl or benzyl optionally mono- or di-substituted, the substituents being selected from the group consisting of
  - (1) hydrogen,
  - (2) $CF_3$,
  - (3) CN,
  - (4) F, Cl, Br or I,
  - (5) $C_{1-4}$alkyl;

$R^{12}$ is
- (a) —$C_{1-3}$ alkyl,
- (b) —$CF_3$,
- (c) phenyl or benzyl optionally mono- or di-substituted, the substituents being selected from the group consisting of
  - (1) hydrogen,
  - (2) $CF_3$, (3) CN,
(4) F, Cl, Br or I,
(5) $C_{1-3}$alkyl.

5. A compound according to claim 4 wherein
Q is
  (a) —OR or
  (b) —$NR^9R^{10}$;
R is
  (a) —H or
  (b) —$C_{1-3}$ alkyl;
$R^1$ is
  (a) —$OCH_3$,
  (b) —$OCH_2F$,
  (c) —$OCHF_2$,
  (d) F, Cl or Br,
  (e) methyl or ethyl;
$R^2$ and $R^3$ are independently
  (a) —H,
  (b) —F,
  (c) methyl or ethyl,
  (d) —$CF_3$;
$R^4$ is
  (a) —H,
  (b) methyl or ethyl,
  (c) —OH or $SR^8$,
  (f) mono- or di-substituted benzyl, wherein the substituent is selected from
    (1) hydrogen,
    (2) $CF_3$,
    (3) CN,
    (4) F, Cl, Br or I,
    (5) $C_{1-3}$alkyl,
    (6) $SR^8$, $S(O)R^8$, or $S(O)_2R^8$,
or $R^2$ and $R^3$ are joined so that together with the carbon atom to which they are attached there is formed a saturated monocyclic hydrocarbon ring of 3, 4, 5, 6 or 7 members;
or $R^3$ and $R^4$ are joined so that together with the carbon atoms to which they are attached there is formed a saturated monocyclic hydrocarbon ring of 3, 4, 5, 6 or 7 members;
$R^5$ is H or methyl;
$R^6$ is H or F;
$R^7$ is
  (a) Br or Cl,
  (b) SMe, SEt, or $SCF_2H$;
$R^8$ is methyl, ethyl or mono- or di-substituted benzyl, wherein the substituent is selected from
  (1) hydrogen,
  (2) $CF_3$,
  (3) CN,
  (4) F, Cl, Br or I,
  (5) $C_{1-3}$alkyl;
$R^9$ is hydrogen or methyl;
$R^{10}$ is
  (a) —H,
  (b) —$C_{1-3}$ alkyl,
  (c) —OR,
  (d) —$C(O)R^{11}$,
  (e) —$S(O)_2R^{12}$,
$R^{11}$ is
  (a) H,
  (b) —$C_{1-3}$ alkyl,
  (c) —$CF_3$,
  (d) phenyl or benzyl optionally mono- or di-substituted, the substituents being selected from the group consisting of
    (1) hydrogen,
    (2) $CF_3$,
    (3) CN,
    (4) F, Cl or Br,
    (5) $C_{1-4}$alkyl;
$R^{12}$ is
  (a) —$C_{1-3}$ alkyl,
  (b) —$CF_3$,
  (c) phenyl or benzyl optionally mono- or di-substituted, the substituents being selected from the group consisting of
    (1) hydrogen,
    (2) $CF_3$,
    (3) CN,
    (4) F, Cl, Br or I,
    (5) $C_{1-3}$alkyl.

6. A compound according to claim 5 wherein
Q is
  (a) —OH
  (a) —$NH_2$, or
  (a) —$NHS(O)_2Me$;
R is
  (a) —H or
  (b) methyl, ethyl, or propyl;
$R^1$ is
  (a) —$OCH_3$,
  (b) Cl or Br;
$R^2$ and $R^3$ are independently
  (a) —H,
  (b) methyl,
  (c) $CF_3$;
$R^4$ is
  (a) —H,
  (b) methyl, or
  (c) benzyl;
or $R^2$ and $R^3$ are joined so that together with the carbon atom to which they are attached there is formed a saturated monocyclic hydrocarbon ring of 3 members;
or $R^3$ and $R^4$ are joined so that together with the carbon atoms to which they are attached there is formed a saturated monocyclic hydrocarbon ring of 3 members;
$R^5$ is H or methyl;
$R^6$ is H;
$R^7$ is Br
$R^9$ is hydrogen;
$R^{10}$ is
  (a) methyl, ethyl, propyl,
  (b) $CH_3$;
$R^{12}$ is
  (a) —$C_{1-3}$ alkyl,
  (a) —$CF_3$.

7. A compound according to claim 1 selected from the group consisting of
(a) 3-[1-(p-Bromobenzyl)-5-methoxy-2-methylindol-3-yl] propanoic acid,
(b) 3-[1-(p-Bromobenzyl)-5-methoxy-2-methylindol-3-yl] butanoic acid,
(c) 2-Benzyl-3-[1-(p-bromobenzyl)-5-methoxy-2-methylindol-3-yl]-propanoic acid,
(d) 3-[1-(p-bromobenzyl)-5-methoxy-2-methylindol-3-yl]-2,2-dimethyl-propanoic acid,
(e) 3-[1-(p-bromobenzyl)-5-methoxy-2-methylindol-3-yl]-4,4,4-trifluoro-butanoic acid,
(f) trans-2-[1-(p-Bromobenzyl)-5-methoxy-2-methylindol-3-yl]-cyclo-propanecarboxylic acid,
(g) 3-[1-(p-Bromobenzyl)-5-methoxy-2-methylindol-3-yl]-3-hydroxy-2-methyl propanoic acid, (h) [1-(1-(p-Bromobenzyl)-5-methoxy-2-methylindol-3-yl)-cyclopropyl]-acetic acid,
(i) trans-(+)-2-[1-(p-Bromobenzyl)-5-methoxy-2-methylindol-3-yl]-cyclopropanecarboxylic acid,
(j) 3-[1-(p-Bromobenzyl)-5-methoxy-2-methylindol-3-yl]-2-methyl-propanoic acid,
(k) 3-[1-(p-Chlorobenzyl)-5-methoxy-2-methylindol-3-yl]-4,4,4-trifluoro-butanoic acid,
(l) syn-3-[1-(p-Bromobenzyl)-5-methoxy-2-methylindol-3-yl]-2-methyl-butanoic acid,
(m) anti-3-[1-(p-Bromobenzyl)-5-methoxy-2-methylindol-3-yl]-2-methyl-butanoic acid and sodium salt,
(n) 3-[5-Bromo-1-(p-bromobenzyl)-2-methylindol-3-yl]butanoic acid,
(o) (−)-3-[1-(p-Bromobenzyl)-5-methoxy-2-methylindol-3-yl]-butanoic acid,
(p) (+)-3-[1-(p-Bromobenzyl)-5-methoxy-2-methylindol-3-yl]-butanoic acid and sodium salt,
(q) trans-(−)-2-[1-(p-Bromobenzyl)-5-methoxy-2-methylindol-3-yl]-cyclopropanecarboxylic acid,
(p) 3-[1-(p-Bromobenzyl)-2,5-dimethylindol-3-yl)propanoic acid,
(r) 3-[5-Bromo-1-(p-bromobenzyl)-2-methylindol-3-yl)propanoic acid,
(s) 3-[1-(p-Bromobenzyl)-5-chloro-2-methylindol-3-yl)propanoic acid,
(t) 3-[1-(p-Chlorobenzyl)-5-methoxy-2-methylindol-3-yl)-2-methyl-propanoic acid,
(u) Methyl 3-[1-(p-bromobenzyl)-5-methoxy-2-methylindol-3-yl)-propanoate,
(v) 3-[1-(p-Bromobenzyl)-5-methoxy-2-methylindol-3-yl]-2-(p-methylthio-benzyl)propanoic acid, and
(w) 3-[1-(p-Bromobenzyl)-5-methoxy-2-methylindol-3-yl)-3-methylbutanoic acid, or a pharmaceutically acceptable salt thereof.

8. A pharmaceutical composition for treating an inflammatory disease susceptable to treatment with an non-steroidal anti-inflammatory agent comprising:
a non-toxic therapeutically effective amount of a compound according to claim 1 and a pharmaceutically acceptable carrier.

9. A pharmaceutical composition for treating cyclooxygenase mediated diseases advantageously treated by an active agent that selectively inhibits COX-2 in preference to COX-1 comprising:
a non-toxic therapeutically effective amount of a compound according to claim 1 and a pharmaceutically acceptable carrier.

10. A method of treating an inflammatory disease susceptible to treatment with an non-steroidal anti-inflammatory agent comprising:
administration to a patient in need of such treatment of a non-toxic therapeutically effective amount of a compound according to claim 1 and a pharmaceutically acceptable carrier.

11. A method of treating cyclooxygenase mediated diseases advantageously treated by an active agent that selectively inhibits COX-2 in preference to COX-1 comprising:
administration to a patient in need of such treatment of a non-toxic therapeutically effective amount of a compound according to claim 1.

12. A method of treating inflammation in a patient for which non-steroidal anti-inflammatory drugs may be contraindicated comprising:
administration to a patient in need of such treatment of a non-toxic therapeutically effective amount of a compound according to claim 1 and a pharmaceutically acceptable carrier.

13. A compound according to claim 1 wherein:
Q is —OH;
$R_1$ is —OCH$_3$;
$R^2$ and $R^3$ are independently
(a) —H,
(b) methyl, or
(c) —CF$_3$;
$R^4$ and $R^5$ are independently
(a) —H, or
(b) methyl;
or $R^2$ and $R^4$ are joined so that together with the carbon atoms to which they are attached there is formed a saturated monocyclic hydrocarbon ring of 3 members;
or $R^2$ and $R^5$ are joined so that together with the carbon atoms to which they are attached there is formed a saturated monocyclic hydrocarbon ring of 3 members;
or $R^3$ and $R^4$ are joined so that together with the carbon atoms to which they are attached there is formed a saturated monocyclic hydrocarbon ring of 3 members;
or $R^3$ and $R^5$ are joined so that together with the carbon atoms to which they are attached there is formed a saturated monocyclic hydrocarbon ring of 3 members;
$R^6$ is H;
$R^7$ is Br, Cl or I.

14. A compound according to claim 13 wherein:
Q is —OH;
$R^1$ is —OCH$_3$;
$R^2$, $R^3$, $R^4$ and $R^5$ are independently
(a) —H, or
(b) methyl;
wherein exactly one of $R^2$, $R^3$, $R^4$ and $R^5$ is methyl;
or $R^2$ and $R^4$ are joined so that together with the carbon atoms to which they are attached there is formed a saturated monocyclic hydrocarbon ring of 3 members;
or $R^2$ and $R^5$ are joined so that together with the carbon atoms to which they are attached there is formed a saturated monocyclic hydrocarbon ring of 3 members;
or $R^3$ and $R^4$ are joined so that together with the carbon atoms to which they are attached there is formed a saturated monocyclic hydrocarbon ring of 3 members;
or $R^3$ and $R^5$ are joined so that together with the carbon atoms to which they are attached there is formed a saturated monocyclic hydrocarbon ring of 3 members;
$R^6$ is —H;
$R^7$ is Br, Cl or I.

15. A compound according to claim 14 wherein:
Q is —OH;
$R^1$ is —OCH$_3$;
$R^2$ and $R^4$ are joined so that together with the carbon atoms to which they are attached there is formed a saturated monocyclic hydrocarbon ring of 3 members;
$R^3$, $R^5$ and $R^6$ are —H;
$R^7$ is Br.

16. A compound according to claim 13 selected from the group consisting of:
(a) 3-[1-(p-bromobenzyl)-5-methoxy-2-methylindol-3-yl]-butanoic acid, sodium salt;
(b) trans-2-[1-(p-bromobenzyl)-5-methoxy-2-methylindol-3-yl]-cyclo-propanecarboxylic acid, sodium salt;
(c) 3-[1-(p-bromobenzyl)-5-methoxy-2-methylindol-3-yl]-4,4,4-trifluorobutanoic acid, sodium salt; and
(d) 3-[1-(p-Bromobenzyl)-5-methoxy-2-methylindol-3-yl]-2-methyl-propanoic acid, sodium salt.

\* \* \* \* \*